United States Patent [19]
Herrera-Estrella et al.

[11] Patent Number: 6,130,366
[45] Date of Patent: *Oct. 10, 2000

[54] CHIMAERIC GENE CODING FOR A TRANSIT PEPTIDE AND A HETEROLOGOUS POLYPEPTIDE

[75] Inventors: Luis Herrera-Estrella; Guidi Van Den Broeck, both of Ghent; Marc Van Montagu, Brussels, all of Belgium; Peter Schreier; Josef Schell, both of Cologne, Germany; Hans J. Bohnert, Tucson, Ariz.; Anthony R. Cashomore, Woodside; Michael P. Timko, New York, both of N.Y.; Albert P. Kausch, Durham, N.H.

[73] Assignees: Plant Genetic Systems, Gent, Belgium; Bayer AG, Leverkusen, Germany

[*] Notice: This patent is subject to a terminal disclaimer.

[21] Appl. No.: 08/984,151

[22] Filed: Dec. 3, 1997

Related U.S. Application Data

[62] Division of application No. 08/430,257, Apr. 28, 1995, Pat. No. 5,728,925, which is a continuation of application No. 08/267,306, Jun. 29, 1994, abandoned, which is a continuation of application No. 08/026,213, Mar. 1, 1993, abandoned, which is a continuation of application No. 07/794,635, Nov. 18, 1991, abandoned, which is a continuation of application No. 07/480,343, Feb. 14, 1990, abandoned, which is a continuation of application No. 06/755,173, Jul. 15, 1985, abandoned.

[30] Foreign Application Priority Data

Dec. 28, 1984 [GB] United Kingdom .................. 84-32757
Jan. 7, 1985 [GB] United Kingdom .................. 85-00336

[51] Int. Cl.[7] ........................... C12N 15/29; C12N 15/62; C12N 15/82; A01H 5/00
[52] U.S. Cl. ....................... 800/278; 435/69.1; 435/69.7; 435/69.8; 435/419; 800/287; 800/288; 800/300; 536/23.4; 536/23.6; 536/24.1; 536/23.7
[58] Field of Search .................................. 435/69.1, 69.7, 435/69.8, 419, 468, 469; 800/287, 288, 278, 300; 536/23.4, 23.6, 24.1, 23.7

[56] References Cited

FOREIGN PATENT DOCUMENTS

| | | |
|---|---|---|
| 0 193259 | of 1986 | European Pat. Off. . |
| 0 218571 | of 1987 | European Pat. Off. . |
| 0 356061 | 2/1990 | European Pat. Off. . |
| WO84/02913 | of 1984 | WIPO . |

OTHER PUBLICATIONS

Hirschberg et al., 1983, Science 222:1347–1349.
Herrera–Estrella et al., 1984, Nature 310:115–120.
DeBlock et al., 1984, EMBO J 3(8):1681–1689.
Ellis et al., pp. 25–39 In: The Enzymology of the Post–Translational Modification of Proteins (Freedman et al., eds) Academic Press, 1985.
Broglie, R. et al., (1984) Science 224:838–843.
Broglie, R. et al., (1983) Biotechnology 1:55–61.
Murai, N. et al. (1983), Science 222:476–482.
Joos H. et al., Cell 32:1057–1067.
Lewin R., 1987, Science 237:1570.
Reeck et al., 1987, Cell 50:667.
Ellis, R. 1984, Chloroplast Biogenesis, University Press, Cambridge, England, pp. 1–9.
Goodman et al., 1987, Science 236:48–54.
Shields, R., 1984, Nature 310:98.
Shields, S., 1985, Nature 317:668.
Schell and Van Montagu, 1986, Molecular Developmental Biology, pp. 3–13.
Schreier et al., 1985, EMBO J. 4(1):25–32.
Cocking et al., 1981, Nature 293(5830):265–270.
Gould et al., Plant Physiol., vol. 95, pp. 426–434 (1991).
Wong et al., Plant Molecular Biology, vol. 20, pp. 81–93 (1992).
Keegstra, Cell, vol. 56, pp. 247–253 (1989).
Oakes et al., Bio/Technology, vol. 9, pp. 982–986 (Oct. 1991).
"Gene Manipulation Plant–Improvement," Stadler Genet., Symp. 16th, pp. 577–603 (1984).
Herrera–Estrella et al., "Photoregulation of Nuclear Gene Expression," Abstracts of papers Presented at the 1984 meeting on "Molecular Biology of the Photosynthetic Apparatus," May 9–May 13, 1984.
Douglas et al., Proc. Natl. Acad. Sci., vol. 81, pp. 3983–3987 (1984).
Hurt et al., FEBS, vol. 178, No. 2, pp. 306–310 (1984).
Kalderon et al., Nature, vol. 311, pp. 33–38 (1984).
Cheung et al., Proc. Natl. Acad. Sci., vol. 85, pp. 391–395 (1988).
Smeekens et al., TIBS, vol. 15, pp. 73–76 (1990).
Horsch et al., Science, vol. 223, p. 496 (1984).
Lewin, R., Science, vol. 237, p. 1570 (1987).
Reeck et al., Cell, vol. 50, pp. 667 (1987).
DeGreve et al. Nature 300: 752–755 1982.
Ellis, R. Chloroplast Biogensis. Cambridge University Press: Cambridge, England, pp. 1–9 1984.

*Primary Examiner*—David T. Fox
*Attorney, Agent, or Firm*—Birch, Stewart, Kolasch & Birch, LLP

[57] ABSTRACT

Chimaeric DNA sequence which encodes: 1) a transmit peptide of a cytoplasmic precursor of a chloroplast protein or polypeptide of a plant and 2) a protein or polypeptide that is heterologous to the transit peptide. The chimaeric DNA sequence can be used as a vector for transforming a plant cell so that a chimaeric precursor of the heterologous protein or polypeptide is produced in the cytoplasm of the cell and the chimaeric precursor then transports the heterologous protein or polypeptide in vivo into a chloroplast of the cell.

49 Claims, 16 Drawing Sheets

-57        -1 ↓ +1

Met... Ser Asn Gly Gly Arg Val Lys Cys Met Gln Val Trp Pro Pro Ile Gly Lys Lys Lys...

Met... Ser Asn Gly Gly Arg Val Lys Cys Met AspPro Ala Asn Leu Ala Trp <u>Ile</u> <u>Glu</u>

CHIMAERIC GENE CODING FOR A TRANSIT PEPTIDE AND A HETEROLOGOUS POLYPEPTIDE

This application is a divisional of application Ser. No. 08/430,257 filed Apr. 28, 1995, now U.S. Pat. No. 5,728,925, which was a continuation of application Ser. No. 08/267,306 filed Jun. 29, 1994, now abandoned, which was a continuation of application Ser. No. 08/026,213 filed Mar. 1, 1993, now abandoned, which was a continuation of application Ser. No. 07/794,635 filed Nov. 18, 1991, now abandoned, which was a continuation of application Ser. No. 07/480,343 filed Feb. 14, 1990, now abandoned, which was a continuation of application Ser. No. 06/755,173 filed Jul. 15, 1985, now abandoned, the entire contents of which are hereby incorporated by reference.

FIELD OF THE INVENTION

The invention relates to means, particular recombinant vectors, and to processes for the controlled introduction of foreign gene products in plant chloroplasts.

The disclosure which follows contains reference numbers in the form of exponents. They refer to bibliographic references relative to literature referred to at the end of this specification. Other literature is also referred to in the course of this description by the name of the first author and date of publications. All the articles as well as the patent applications, patents, etc., which shall be referred to throughout this specification are incorporated herein by reference.

It is well known that the cells of eukaryotic organisms, and more particularly plant cells, contain distinct subcellular compartments, or organelles, delimited by characteristic membrane systems and performing specialized functions within the cell. In photosynthetic leaf cells of higher plants the most conspicuous organelles are the chloroplasts, which exist in a semi-autonomous fashion within the cell, containing their own genetic system and protein synthesis machinery, but relying upon a close cooperation with the nucleo-cytoplasmic system in their development and biosynthetic activities[1].

The most essential function of chloroplasts is the performance of the light-driven reactions of photosynthesis. But chloroplasts also carry out many other biosynthetic processes of importance to the plant cell. For example, all of the cell's fatty acids are made by enzymes located in the chloroplast stroma, using the ATP, NAOPH, and carbohydrates readily available there. Moreover, the reducing power of light activated electrons drives the reduction of nitrite $NO^-_2$) to ammonia ($NH_3$) in the chloroplast; this ammonia provides the plant with nitrogen required for the synthesis of amino acids and nucleotides.

The chloroplast also takes part in processes of particular concern to the agrochemical industry.

Particularly it is known that many herbicides act by blocking functions which are performed within the chloroplast. Recent studies have identified the specific target of several herbicides. For instance, triazine derived herbicides inhibit photosynthesis by displacing a plastoquinone molecule from its binding site in the 32 Kd polypeptide of the photosystem II. This 32 Kd polypeptide is encoded in the chloroplast genome and synthesized by the organelle machinery. Mutant plants have been obtained which are resistant to triazine herbicides. These plants contain a mutant 32 Kd protein from which the plastoquinone can no longer be displace by triazine herbicides.

Several other herbicides are known to block specific steps in amino acids synthesis. Sulfonyl-uras are known to inhibit acetolactate synthase. This enzyme is involved in isoleucine and valine synthesis. Glyphosate inhibits the function of 5-enol pyruvyl-3-phosphoshikimate synthase, which is an enzyme involved in the synthesis of aromatic amino acids. All these enzymes are encoded by the nuclear genome, but they are translocated into the chloroplast where the actual amino acids synthesis takes place.

Enzymes responsible for the same functions are also present in prokaryotes. It should be easy to obtain bacterial mutants in which the enzyme of interest is no longer sensitive to the herbicide. Such a strategy was used with success to isolate *Salmonella typhimurium* mutants with an altered aro A gene product, which confers resistance to glyphosate (Comai et al Science 221, 370 (1983).

Thus the use of chloroplastic or bacterial genes to confer herbicide resistance to plant cells could be successful if their gene products were efficiently transported into the chloroplast where they function.

Chloroplasts are also involved in the complex mechanisms which regulate the levels of amino acids synthesis. One of the most important regulatory mechanisms is the so-called retroregulation. This mechanism involves the inhibition of the key enzyme of a given pathway by the end product(s) of this pathway. When a key enzyme is no longer subjected to such regulation the organism overproduces the corresponding end product (e.g., an amino acid).

Isolation of mutant genes encoding for enzymes that are insensitive to inhibition by the corresponding end product is well documented in bacteria. Similar mutants in plant cells are difficult to obtain and only a few examples have been reported. Furthermore the isolation of genes from plant cells is a very complex task when compared to the isolation of bacterial genes.

As mentioned earlier, most amino acids synthesis take place inside the chloroplast.

Thus, there is a great interest for the development of a technique for transforming plant cells with bacterial genes encoding an enzyme insensitive to inhibition by the above-said end product in a way such that the result of this transformation process would be the introduction of said enzyme in the plant chloroplasts. The ultimate result of this process would be an over-production of amino acid.

These are but a few examples (additional examples will be mentioned later) of the prospects of considerable development of plant genetic engineering which will be at hand for the specialists as soon as practical techniques suitable for the introduction of determined foreign polypeptides or proteins in chloroplasts become available.

Indeed, many techniques have been proposed for the transfer of DNA to plants such as direct DNA uptake, micro-injection of pure DNA and the use of viral or plasmid vectors. Plasmid vectors which have proven particularly efficient are those derived from tumor-inducing (Ti) plasmids of the microorganism *Agrobacterium tumefaciens* which is the agent of crown gall disease in dicotyledonous plants. Those plasmids can be modified by removal of the tumor-causing genes from their T-DNA. The so modified plasmids then no longer interfere with normal plant growth and differentiation and, upon insertion of a determined foreign gene at an appropriate site of said plasmids, can be used for promoting the expression of the protein encoded by said determined gene in plant cells. Particularly, the foreign gene may be inserted close to one of the border sequences or between the two border sequences which surround the T-DNA in intact Ti-plasmids. Reference can be made by way of examples to the articles of:

A. CAPLAN et al. titled "Introduction of Genetic Material into Plant Cells", Science, Nov. 18, 1983, volume 222, pp. 815–812;

O. HERRERA-ESTRELLA et al. titled "Expression of chimaeric genes transferred into plant genes using a Ti-plasmid-derived vectors", Nature, Vol. 303, No. 5914, pp. 209–213, May 13, 1983;

L. HERRERA-ESTRELLA et al. titled "Light-inducible and chloroplast associated expression of a chimaeric gene introduced into *Nicotiana tabacum* using a Ti-plasmid vector", Nature, vol. 310, n+ 5973, pp. 115–120, Jul. 12, 1984;

or to European Patent Application N+ 0 116 718 (or to U.S. application Ser. No. 570,646) or to the International Application WO 84/02913 published under the PCT;

all of these articles or patent applications being incorporated herein by reference.

Yet all of these techniques do not provide an efficient and relatively easy method of transformation of chloroplasts, despite the considerable work which has been devoted to the subject and the already large amount of knowledge which has been acquired, particularly concerning the production of proteins in plant cells and transfer into the chloroplasts. As a matter of fact vectors for the direct transformation of chloroplasts are unavailable at this time. Furthermore mature proteins, including those normally encoded in the plant cells including said chloroplasts and which can ultimately be isolated naturally from said chloroplasts, cannot as such be caused to penetrate in the chloroplasts if supplied thereto from outside.

Most chloroplast proteins are coded for in the nuclear DNA and are the products of protein synthesis on cytoplasmic ribosomes, many as soluble higher molecular weight precursors[2–9]. These precursors are then translocated through either one or both of the plastid envelope membranes, processed, and assembled into their final organellar compartment or holoenzyme complex. In vitro reconstitution experiments using isolated chloroplasts, have demonstrated that the uptake and processing of over one hundred nuclear-encoded, cytoplasmically synthesized precursors by chloroplasts occurs by an energy-dependent[17], post-translational mechanism [6, 10–17].

The most extensively characterized of these nuclear-encoded chloroplast proteins is the small subunit of ribulose-1,5-bisphosphate (RuBP) carboxylase. This polypeptide is synthesized on free cytoplasmic ribosomes as a precursor of 20,000 daltons containing an amino terminal extension or transit peptide of approximately 5–6,000 daltons[6–7, 9]. During or immediately after import of the precursor into the chloroplast, the transit peptide is proteolytically removed in two steps by a soluble protease[18], yielding a mature small subunit polypeptide of 15,000 daltons. This polypeptide is then assembled with an endogenous large subunit into the functional RuBP carboxylase holoenzyme[11,12].

Similar observations were made with the chlorophyl a/b binding proteins. These polypeptides are synthesized as soluble precursors on cytoplasmid ribosomes (Apel and Kloppstech, 1978; Schmidt et al., 1981) and are post-translationally translocated into chloroplasts. During or after translocation the $NH_2$-terminal transit peptides are proteolytically cleaved (Schmidt et al., 1981) to yield the mature polypeptides. The mature A and B polypeptides associated with chlorophyl a and b are integrated into the thylakoid membrane. The transit peptides of post-translationally transported chloroplast proteins are characterized by a preponderance of basic amino acids, a feature which has been proposed as important in the interaction of the transit peptide with the chloroplast envelope[19]. Comparison of transit peptides of small sub-unit precursors from various plant species show a variation in amino acid sequence, but a relatively strong conservation in the position of prolines and charged amino acid residues [20–22] and a substantial homology in a region surrounding the cleavage site of the precursors, as observed in soybean (Berry-Lowe et al.; 1982) pea (Cashmore, 1983), duck weed (Stiekema et al., 1983) and wheat (Broglie et al.; 1983). These common properties may be of functional significance since both in vitro[11,12] and in vivo[23], the small subunit precursors from one plant species can be imported and correctly processes by the chloroplasts of others and vice-versa.

The molecular basis of how the post-translational translocation of polypeptides into chloroplasts occurs and which signals are involved in this process, more particularly the relative contributions of the transit peptide and the mature protein to the uptake and processing mechanism are still not fully understood, even though it was already presumed that the transit peptide is required for the translocation of the mature protein. Consistent with this is the observation that the mature small subunit protein is not translocated into chloroplasts[24].

The invention stems from several discoveries which have been made by Applicants, as a result of further studies of the translocation mechanisms through the chloroplast membranes of chloroplast-protein precursors encoded by the nuclear DNA of plant cells. It seems that not cytoplasmic factor is required for the translocation mechanism itself as a result of further studies carried out on RuBP.

Further it has been found that all the sequence information required for translocation and transport of the mature protein or of a subunit thereof through the chloroplast membranes seems to reside within the precursor subunits and even within the sole transit peptides normally associated therewith. It further appeared that transit peptides not only mediate translocation, but also include information necessary for site-specific processing of the corresponding proteins.

These different properties of the transit peptides are at the basis of the recombinant DNAs, more particularly recombinant vectors including a DNA sequence coding for a determined protein or polypeptide, particularly a foreign protein, sought to be introduced and processed in chloroplasts, as well as the processes for the introduction of such foreign polypeptide or protein into the chloroplasts, for instance in the thylacoid membranes or, preferably, in the stroma thereof. As a matter of fact an essential element of these recombinant vectors consists of a DNA sequence coding for a transit peptide, it being understood that this expression, as used throughout this specification and claims attached thereto, designates the amino acid sequence contained in any chloroplast protein precursor which, upon import of the precursor, is proteolytically removed during or immediately after import of the precursor into the chloroplast to yield either the corresponding functional mature protein or a subunit thereof, particularly when, like in the case of RuBP, the final processing of the mature protein takes place within the chloroplast. Such final processing comprises, for instance, the assembling of said subunit with another endogenous subunit to yield the final functional protein.

SUMMARY OF THE INVENTION

The recombinant DNA according to the invention which can be introduced into plant cells is characterized by the presence therein of a chimaeric gene comprising a first nucleic acid and a second nucleic acid recombined with each other, said first nucleic acid and said second nucleic acid being of different origins, particularly being foreign to each other, wherein said first nucleic acid contains a first coding sequence which has essential sequence homology with a natural gene sequence coding for a transit peptide belonging to a precursor comprising at least the N-terminal sub-unit of a chloroplast protein capable of being transported into or processed within the chloroplast of said plant cells and wherein said second nucleic acid contains a second coding sequence-distinct of the gene sequence coding for said chloroplast protein or chloroplast protein sub-unit, said second nucleic acid being located downstream of said first nucleic acid in the direction of the transcription of their first and second sequences respectively.

DESCRIPTION OF THE PREFERRED EMBODIMENTS

Figure 1A:
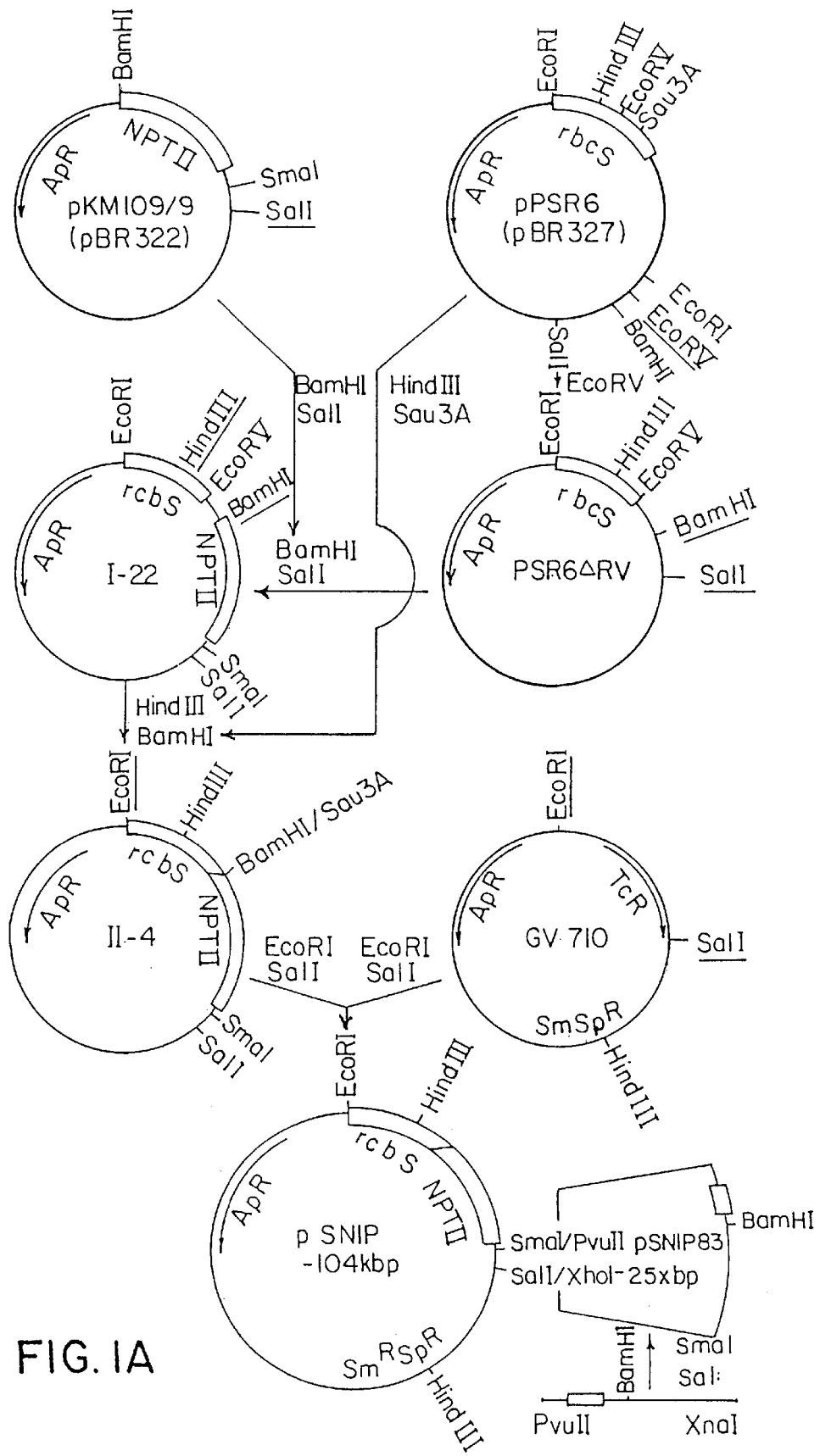
FIG. 1A diagrammatically represents the successive steps of the construction of preferred recombinant DNAs, including a vector suitable for the transformation of plant cells, containing a chimaeric gene according to a first preferred embodiment of this invention.

In joint efforts of the inventors to solve the problem sought, i.e., providing methods and means for transporting a protein into chloroplasts, the inventors have devised two main approaches which have in common the use of recombinant DNAs including a sequence coding for a transit peptide. These two approaches resulted in the two preferred embodiments which will be exemplified hereafter and which both proved to be effective.

Example I is illustrative of the first approach which took into account the possibility that a larger part of the nuclear genes, including the entire region of high homology around the cleavage site of the precursors would be a necessary requirement for transport and processing of proteins, particularly foreign proteins, into chloroplasts. This resulted in a first series of preferred recombinant DNAs of this invention more particularly characterized in that the first nucleic acid as defined hereabove contains a third sequence corresponding to at least part of a nucleic acid encoding the N-terminal cytoplasmic subunit of a chloroplast protein downstream of said first sequence and in that the extremity of said third sequence is substantially contiguous to the extremity of said first nucleic acid.

Preferably the third sequence does not extend beyond the nucleotides encoding the N-terminal extremity of the cytoplasmic subunit of said chloroplast protein, yet it comprises an intron, particularly that which initially belonged to the same gene as the exons encoding the peptidic portions which will ultimately provide the precursor subunit of the corresponding natural chloroplast protein.

It will be seen that a preferred embodiment of a recombinant DNA corresponding to the abovesaid first approach includes a first sequence encoding the transit peptide and a third sequence which initially belonged to the same gene and which encodes the first 22 amino acids of the small subunit gene (rbcS) from *Pisium sativum* (Cashmore, 1983), said third gene being then fused to the coding region of a foreign protein, such as the nptII gene which codes for neomycine phosphotransferase II (npt(II) gene obtained from a Tn5 transposon).

Example II is illustrative of the construction which can be made upon taking the second approach to solve the same problems. In this construction, the nptII coding sequence is fused directly to the transit peptide coding sequence such that the potential protein cleavage site does not contain any amino acids derived from the mature small subunit protein except the methionine following the last amino acid of the transit peptide. More generally, and preferably, the first codon of the second sequence (encoding the protein, particularly a foreign protein, which is sought to be translocated into the chloroplasts) is immediately adjacent to the last codon of said first DNA sequence coding for said transit peptide. Thus, particularly when the abovesaid second sequence encodes a polypeptide or protein different from the chloroplast protein normally associated with the transit peptide encoded by said first sequence, the nucleotide sequence next to said first sequence in said chimaeric gene is generally (possibly except for a first codon coding for methionine) by free of sequence homology with the nucleotide sequence encoding the N-terminal part of the normal chloroplast protein. Yet, the last codon of the first sequence and the first codon of the second sequence may be separated by any number of nucleotide triplets, preferably in the absence of any intron of stop codon. For instance, a "third sequence" encoding the first amino acids of the mature protein normally associated with the transit peptide concerned in the corresponding natural precursor (particularly those encoded by the exon containing the first sequence encoding said transit peptide) may be present between said first and second sequences. This "third sequence" may consist of the region of high homology which the N-terminal parts of cytoplasmic precursor-subunits of chloroplast proteins from soybean, pea, duck-weed and wheat have in common. For instance such "third sequence" (be it in the constructions resulting from the "first approach" or those from the "second approach" considered hereabove) encodes the pentapeptide sequence M-Q-V-W-P. These letters correspond to the standard one-letter-abbreviated designations of the natural amino acids. Obviously other "third seqeuences" of nucleotide-sequences can be contemplated upstream or/and also downstream of the above-defined second sequence to the extend where the amino acid sequences encoded are not likely to alter significantly the biological properties of the hybrid protein then formed and translocated into the chloroplasts. Yet in most preferred constructions according to that type the second sequence is preferably fused in phase-register with the first sequence directly contiguous thereto as mentioned earlier or separated therefrom by no more than a short peptide sequence, such as that encoded by a synthetic nucleotide-linker possibly used for achieving the fusion. As shown by Example II such a construction is then capable of ensuring the translocation into the chloroplasts of any protein or protein fragment of controlled amino acid sequence, for instance a bacterial protein or protein fragment or a synthetic polypeptide free of hybridization with any determined peptidic sequence also possessed by a chloroplast protein or precursor.

It must be understood that in the preceding definitions "transit peptide" has the broad meaning indicated hereabove. The transit peptide may further be selected depending upon the plant species which is to be transformed, although, as mentioned earlier, transit peptides or smaller sub-unit precursors containing such transit peptides are often not plant-specific. Sub-unit precursor from one plant species can often be imported and directly processed by the chloroplasts of another.

Preferred DNA sequences encoding a transit peptide for use in the recombinant DNAs of this invention correspond to any of those encoding a transit peptide associated with the small sub-unit of RuBP of pea cells, or also of wheat or soybean cells.

Preferred "first nucleotide sequences" coding for transit peptides are defined hereafter, merely by way of example. It must be understood that the letters above the lines referring to the nucleotide sequence per se designate the successive amino acids encoded by the successive triplets of the nucleotide sequence. The letters below said line correspond to designations of nucleotides which can be substituted for those designated immediately above them in the nucleotide sequence:

```
M   A   S   M   I   S   S   S   A   V   T   T
ATG GCT TCT ATG ATA TCC TCT TCC GCT GTG ACA ACA

V   S   R   A   S   R   G   Q   S   A   A   V
GTC AGC CGT GCC TCT AGG GGG CAA TCC GCC GCA GTG
             T       T                   G

A   P   F   G   G   L   K   S   M   T   G   F
GCT CCA TTC GGC GGC CTC AAA TCC ATG ACT GGA TTC
                         G

P   V   K   K   V   N   T   D   I   T   S   I
CCA GTG AAG AAG GTC AAC ACT GAC ATT ACT TCC ATT

T   S   N   G   G   R   V   K   C
ACA AGC AAT GGT GGA AGA GTA AAG TGC
```

Of course DNA sequences coding for other transit peptides can also be used for the construction of the chimaeric gene of this invention. For instance "first sequences" within the meaning of this application may consist of a sequence encoding the transit peptide of the light harvesting chlorophyl a/b-protein complex, normally located in thylakoid membranes, such as:

```
M   A   A   S   S   S   S   M   A   L   S
ATG GCC GCA TCA TCA TCA TCA TCC ATG GCT CTC TCT

S   P   T   L   A   G   K   Q   L   K   L   N
TCT CCA ACC TTG GCT GGC AAG CAA CTC AAG CTG AAC

P   S   S   Q   E   L   G   A   A   R   F   T
CCA TCA AGC CAA GAA TTG GGA GCT GCA AGG TTC ACC
```

The DNA sequence coding for the transit peptide is advantageously the natural nuclear DNA gene portion or a cDNA obtained from the corresponding mRNA.

Needless to say that any other DNA sequence encoding similar aminoacid sequences can be substituted therefor. It may for instance be contemplated to use a synthetically produced DNA sequence in which some of the codons differ from corresponding codons in the natural DNA sequence, while nevertheless coding for the same corresponding aminoacids. In that respect the expression "transit peptide" should also be understood as extending to any peptide which could differ from a natural transit peptide at the level of some of the aminoacids, to the extent where the substitutions contemplated would not alter the operability of the resulting peptide to promote the translocation into the chloroplast of the foreign polypeptide or protein encoded by the DNA sequence associated with or adjacent to the sequence encoding such peptide. Thus, the chimaeric genes of the invention may be constructed with any "first sequence" having substantial sequence homology with a natural DNA sequence encoding a natural transit peptide.

Concerning the protein or polypeptide encoded by the abovesaid "second sequence", it should also be understood that it may consist of any protein or polypeptide sought to be introduced into or processed within the chloroplasts of determined plants. Therefore the DNA sequence encoding it is usually foreign to or heterologous with respect to the DNA sequence encoding the polypeptide or protein normally associated with the chosen transit peptide. In other words, the first and second DNA sequences usually originate from different sources. Particularly the second sequence encodes a foreign protein or polypeptide, for instance, of bacterial origin. But, the invention also extends to proteins that are naturally endogenous to chloroplasts of plants other than the "determined plant" considered hereabove or even to chloroplast proteins corresponding to natural chloroplast proteins of the same plant, yet differing therefrom only by a few amino acids ("mutated" protein). Techniques for directing such mutation (whether in the first or the second sequences) are exemplified in a recent paper of S. Gutteridge et al. titled "A site specific mutation within the active site of ribulose-1,5-bisphosphate carboxylase of "Rhodospirillum rubrum" (1984).

Furthermore the chimaeric gene of a preferred recombinant DNA according to the invention comprises a promoter region upstream of the above mentioned fused sequences, in such manner that, when said chimaeric gene is inserted within an appropriate vector, the transcription of both the abovesaid first and second sequences are under the control of said promoter. The promoter region contemplated hereabove should of course be selected among those which are recognized by the polymerases endogenous to the plant sought to be transformed. Of particular advantage are the promoters effective in pea, wheat, soybean or tobacco cells. The promoter may be that normally associated with the sequence encoding the chosen transit peptide. It may however also be different. An example of construction using another promoter is illustrated later in the examples. For instance, suitable promoters are those belonging to the genes of plastocyanin, ferredoxin-NADP+ oxydoreductase, etc. Other suitable promoters are exemplified in the literature referred to in this application.

Preferably the sequence coding for the transit peptide is under the direct control of the selected promoter. This means that the first nucleotide triplet transcribed and expressed under the control of said promoter is preferably that of the sequence encoding the transit peptide. This of course is not critical, for instance, as evidenced by the first example.

Finally the invention also relates to recombinant vectors, particularly plasmids which can be introduced and maintained in plant cells and containing the abovesaid chimaeric gene, including the above-defined promoter region.

Preferred vectors of this type are those derived from the Ti-plasmids referred to hereabove. More particularly, a preferred vector of this type comprises in addition to said chimaeric gene a DNA fragment suitably positioned with respect to said foreign gene and having essential sequence homology with the DNA of a Ti plasmid including a T-DNA fragment, the sequences encoding the essential functions capable of causing the transfer of said T-DNA fragment and said chimeric gene into said plant cells. Particularly, a preferred vector according to the invention contains a T-DNA border sequence and said chimaeric gene is positioned close thereto. Even more preferred vectors of this type comprise two border sequences, the chimaeric gene then being positioned between these two border sequences. Concerning general methods for inserting the chimaeric gene in Ti-plasmids, reference is made to the patents referred to above by way of examples.

Advantageously the recombinant DNA (be it the chimaeric gene as such or the vector which contains it) should preferably include the appropriate site for the initiation of the corresponding RNA transcription upstream of the first condon to be translated, in most cases an ATG codon. It is also of advantage that the recombinant DNA comprises downstream of the foreign gene to be expressed appropriate transcription termination and polyadenylation signals.

The invention also concerns a process for achieving and controlling the introduction of a determined protein or polypeptide (or fragment of said protein or polypeptide) into the chloroplasts of determined plant cells. Any suitable process for performing this introduction can be resorted to. Advantageously use is made of vectors of the type exemplified and modified by a chimaeric gene according to the invention and comprising a "second coding sequence" encoding a protein or polypeptide. But any other process can be resorted to. For instance a chimaeric gene according to the invention can be inserted in plant cells simply by the calcium chloride polyethylenglyco) precipitation methods or also by microinjection into the plant cells.

Additional features of the invention will appear in the course of the following disclosure of the conditions under which the structural requirements of vectors capable of transforming plant cells for the sake of ultimately causing a determined foreign gene product to be inserted in chloroplasts were determined.

In the examples which follow the approach taken has been to construct a chimaeric gene encoding a fusion protein containing the transit peptide of the precursor to the small sub-unit of RuBP carboxylase from pea and a coding sequence of the bacterial neomycin phosphotransferase (II) (abbreviated as NPT(II)).

The NPT(II) protein was chosen because NPT(II) protein confers resistance for kanamycin to plants (HERRERA-ESTRELLA et al., 1983: FRALEY et al., 1983; BEVAN et al., 1983), fusion proteins are biologically active (Reiss et al. 1984b) and an enzymatic assay for in situ detection of NPT(II) or NPT(II) fusion proteins in non-denaturing polyacrylamide gels has been described recently[47]. This method is particularly useful to distinguish processed from unprocessed forms of the fusion protein.

EXAMPLE I

GENERAL OUTLINE

Construction of plasmids pSNIP and pSNIF containing the chimaeric gene (tp-ss-nptII)

A genomic clone for one of the rbcS genes from pea was isolated, sequenced and made available by Dr. A. CASHMORE, Rockefeller University, New York (pPSR6). From this clone the promoter signals, (CASHMORE, 1983: HERRERA-ESTRELLA et al., 1984), the first exon coding for the rbcS transit peptide and the first two codons of the mature small subunit protein, followed by the first intron (83 pb) and part of the second exon (66 bp) coding for the amino terminus of the mature small subunit protein were fused via a Sau3A restriction and endonuclease recognition site with the BamHI site of the plasmid pKm109/9 (REISS et al., 1984b) which contains the coding region for the nptII gene from Tn5 (BECK et al., 1982).

The fusion gene which was obtained and which contained the transit sequence (56 codons) and 22 codons from the mature rbcS gene linked via seven artificial codons with the second codon from the nptII gene (FIG. 1B) were found to be similarily active. The size of the coding region of the nptII gene is 1130 bp. The fusion junction was verified (data not shown) by DNA sequencing (MAXAM and GILBERT, 1977). The chimaeric protein should have a size of Mr 38,023 in the unprocessed and of Mr 32,298 in the processed form. Southern type (SOUTHERN, 1975) hybridization data (FIG. 2) established that transformed plant tissues contained the chimaeric gene constructs in the nuclear DNA and that no detectable DNA rearrangements had occured during integration. A schematic representation of the results is given in FIG. 3.

A more detailed disclosure of the construction will be given hereafter, more particularly in relation to FIGS. 1A, 1B and 3.

Production of vectors capable of transforming plants

To introduce the chimaeric genes in the nuclear genomo of plants, the plasmid was inserted into the T-DNA of pGV3851 and of pGV3850, both derivatives of the Ti plasmid pTIC58, in which parts of the T-DNA where substituted by pBR322 (ZAMBRYSKI et al., 1983; 1984). The T-DNA of pGV3851 still contains the genes coding for transcripts 4, 6a and 6b (WILLMITZER et al., 1983) which results in a teratoma-like growth of the transformed tissue (JOOS et al., 1983), whereas all tumor controlling genes have been eliminated in pGV3850 with the result that plant cells transformed with this vector can differentiate and grow as normal plants (ZAMBRYSKI et al., 1983; D E BLOCK et al., 1984). The gene constructions were introduced into pGV3850 and pGV3851 Ti-plasmids by homologous recombination after mobilization from E. coli to Agrobacterium with the help of plasmids R64drd11 and J G28 (VAN HAUTE et al., 1983).

Cointegrates were selected on spectinomycin and streptomycin containing plates and their structure verified by Southern blot hybridization (SOUTHERN, 1975) using various parts of the constructions as probes (data not shown).

Plant transformation

The chimaeric genes were introduced into Nicotiana tabacum cv. Wisconsin 38 or SR1 by inoculation of a wounded plantlet or by co-cultivation of protoplasts with Agrobacterium. Transformed material obtained by wounding was screened for the presence of nopaline synthase activity (OTTEN, 1982), a cotransferred marker. Transformants (pGV3851::pSNIP) grew on 250 ug/ml kanamycin as green teratoma tissue, suggesting that a functional chimaeric gene was present and transcribed. In co-cultivation experiments N. tabacum SR1 protoplasts were incubated with Agrobacterium containing (pGV3850::SNIF) and selected after two weeks with 100 ug/ml kanamycin. From 9 individual colonies which were positive when tested for NPTII activity, one was chosen and regenerated under constant selected pressure to a fully normal looking plant. Genetic analysis shows inheritance of the NPTII marker in a classical mendelian fashion. These results suggested that transcripts from the chimaeric genes were properly processed, transported out of the nucleus and translated into a functionally active protein.

Light induction of the chimaeric gene

Figure 4:
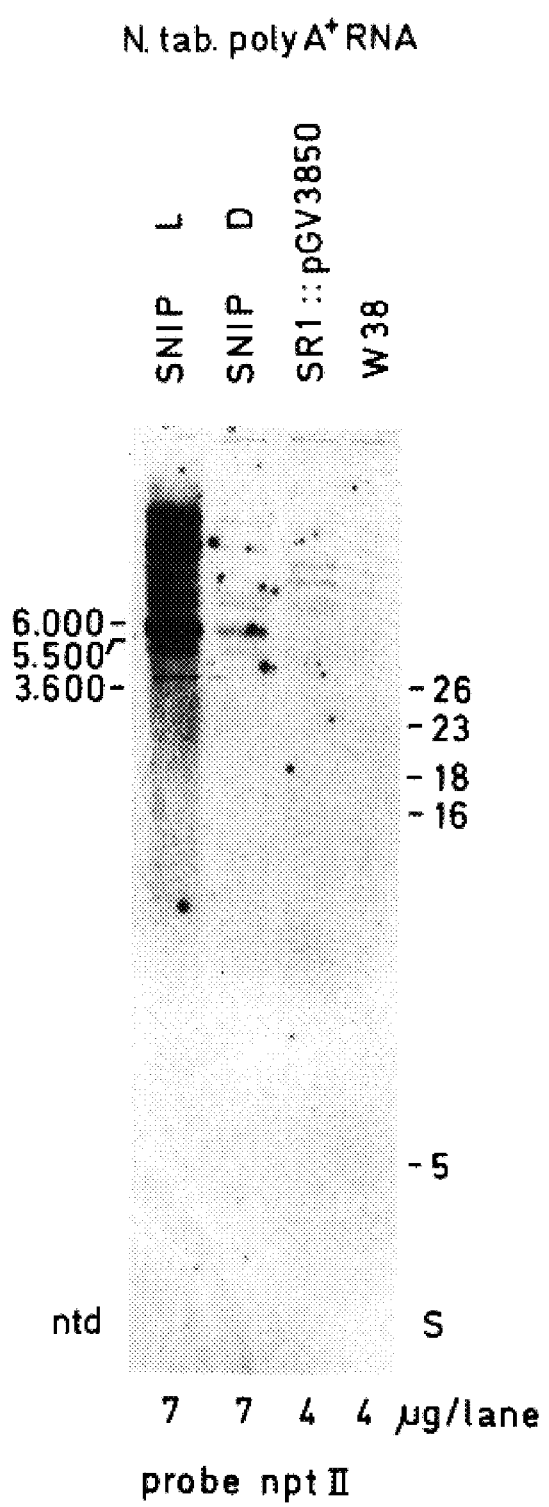
FIG. 4 shows the results obtained in RNA-hybridization experiments carried out in relation to the detection of the transcriptional activity of the promoter included in the chimaeric gene of the invention.
Figure 5A:
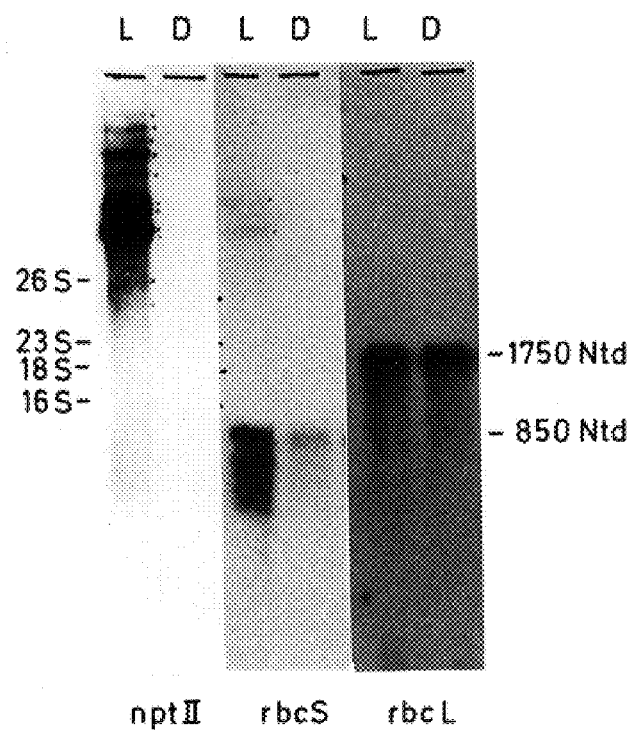
FIGS. 5A and 5B show comparative results of transcription experiments under the control of a light-dependent promoter in plant materials transformed by the recombinant DNAs of the invention.
Figure 5B:
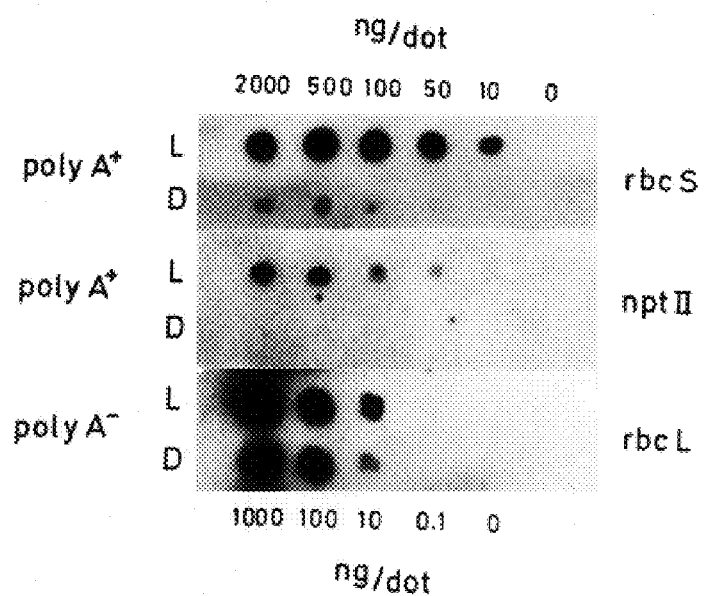

Poly (A)+ and poly (A)−RNA from wild type and from transformed tissues (pGV3851::pSNIP) was isolated and analysed by so called "Northern" gel hybridizations. When the coding region of the nptII gene (BamHI-SmaI fragment from pKM109/9) was used as a probe a complex hybridization pattern was observed with RNAs ranging between 5,500 nucleotides and 8,000 nucleotides in size. These RNAs were detected in light grown teratomas only. Four days of darkness after a day:night rhythm of twelve hours resulted in a marked decrease of the signals (FIG. 4). The very large size of these transcripts probably results from the fact that no proper polyadenylation and transcription termination site was introduced near the translation termination signal. No signals of comparable size or strength were observed in wild type Wisconsin 38 tobacco or in material obtained from a plant transformed with the pGV3850 vector only (FIG. 4). In order to compare the light dependent transcription of the chimaeric gene with that of both the endogenous rbcS gene and the chloroplast gene coding for the large subunit of Rubisco (rbcL), poly (A)+ and poly (A)−RNA from light- and dark-grown teratoma were hybridized to specific probes for each of these genes. The results are illustrated in FIG. 5A. Signals of the endogenous rbcS transcripts (850 nucleotides) were observed at the expected position. Similarly, a transcript of 1750 nucleotides was observed when a rbcL specific probe was used (ZURAWSKI et al.; 1981). The results suggest that the promotor of the rbcL gene, which resides in the chloroplasts, is less sensitive to light stimuli than both the endogenous rbcS and the newly introduced chimaeric gene. Dot blot experiments were included to quantify these results (FIG. 5B). The same probes were used as mentioned before. Individual dots were cut out and the radioactivity counted. A difference of about 25-fold was measured between poly (A)+ RNA from light- and dark-grown teratoma shoots probed with either rbcS or nptII sequences. In contrast, the difference is only 5-fold for poly (A)− RNA specific for rbcL sequences. These results support the Northern experiments indicating that the transcripts of the chloroplast gene coding for the large subunit is less sensitive to influence of light in comparison with the nuclear gene for the small subunit. In addition, it seems that the pea rbcS promotor of the introduced chimaeric gene has a sensitivity to different light regimes which is comparable to that of the endogenous promotor or promotors measured in the tobacco teratoma tissue.

Features of fusion proteins

Figure 6A:
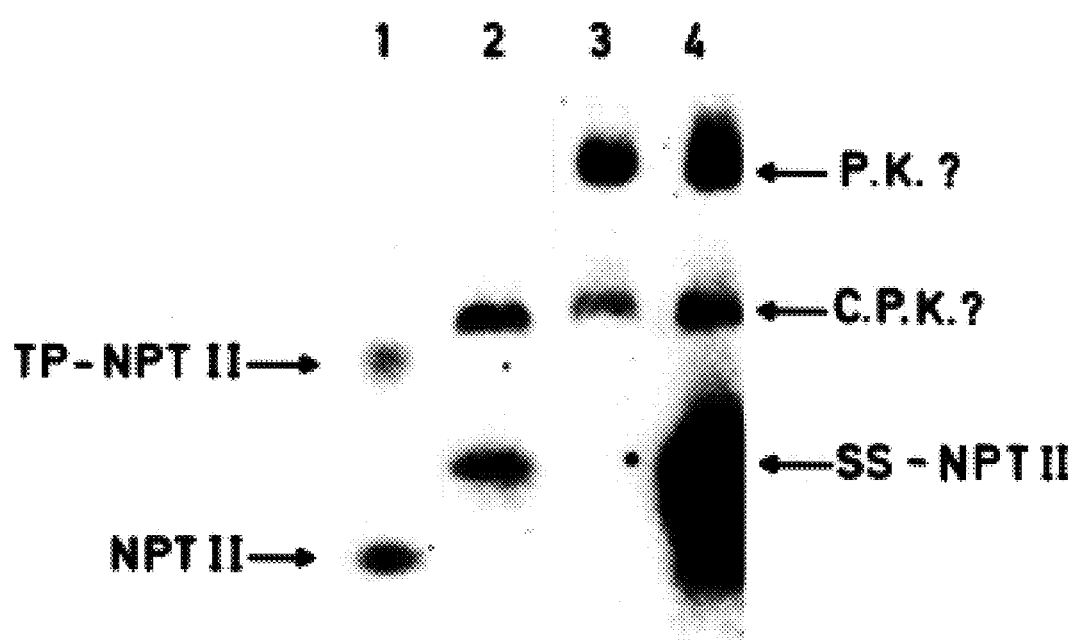
FIG. 6A is representative of the results obtained in experiments purporting to demonstrate the transport of the products encoded by the above said chimaeric gene into the chloroplasts of plant cells.

In order to detect the fusion protein formed between the transit peptide, the $NH_2$-terminal region of the mature small subunit and the NPTII protein in plants, an assay detecting the phosphotransferase-II activity in crude extracts of plants was developed. The method was adapted from published procedures (REISS et al., 1984a) and eliminates most of the endogenous self-phosphorylating proteins which interfere with the assay by proteinase K treatment. The results presented in FIG. 6 demonstrate that NPTII activity is detected in a crude extract (lane 4) of leaves of tobacco plants containing the pGV3850:: pSNIF construct. The activity migrates in the gel assay with a mobility which is intermediate between that of the TP-NPTII fusion protein (35.5 kd) and that of the normal NPTII PROTEIN (29 kd) from extracts of E. coli (lane 1). The relative mobility of the NPTII activity in lane 4 is consistent with a conclusion that it represents the processed form of the precursor protein (SS-NPTII) which has a theoretical molecular weight of 32,298. Since the polarity index (CAPALDI and VANDERKOOI; 1972) of the three proteins is 41 for NPTII, 40 for SS-NPTII and 41 for TP-NPTII, it is legitimate to compare the three proteins by their mobility on native polyacrylamide gels (see FIG. 6B). Indeed the unprocessed TP-SS-NPTII protein has a molecular weight of about 38,000 and would therefore presumably migrate more slowly than the TP-NPTII marker, the SS-NPTII fusion protein is degraded in vitro after isolation yielding active subfragments with a mobility which approaches that of the normal NPTII enzyme. That the lower molecular weight spots seen in FIGS. 6A and 7 are due to unspecific degradation was shown by demonstrating that this and other NPTII fusion proteins are actually degraded in vitro in both bacterial and plant extracts (data not shown). Incubation in the presence of protease inhibitors could not completely prevent this degradation. No activity was detected in control extracts from tobacco lacking the TP-SS-NPTII chimaeric gene (lane 3). The SS-NPTII activity observed in crude extracts can also be detected in isolated chloroplasts (lane 2). The relative amount of activity detected in the chloroplats is significantly less than the activity observed in crude extracts. This is probably due to leakage of the activity out of the chloroplasts during chloroplast isolation. Indeed the procedure used to isolate chloroplasts led, with this particular plant material, to a substantial damage of the chloroplasts. More than 90% of the chloroplast material is either visibly damaged or runs at a reduced density in the percoll gradients. Further manipulations during recovery and concentration prior to the NPTII assay could contribute to further minor damage leading to significant loss of the protein by leakage. These observations do not exclude the possibility that although all of the precursor TP-SS-NPTII protein is processed to the SS-NPTII form, it is not actually all transported in vivo into the stroma of the chloroplasts. However the data obtained clearly demonstrate that at least some of the processed SS-NPTII protein is within the stromal fraction of the chloroplasts. Indeed the activity associated with the chloroplasts was shown to be located within the stroma by demonstrating that broken chloroplasts did not contain any detectable NPTII activity and that the NPTII activity in intact chloroplasts could not be eliminated by trypsin treatment (data not shown). Further evidence that the detected SS-NPTII activity was derived from the introduced light inducible chimaeric gene was obtained by demonstrating that the activity was significantly reduced when tobacco plants containing the pGV3850::pSNIF construct and grown in the green house in a 12 hour light/dark regime (FIG. 7, lane 3) were transferred for 96 hours to complete darkness (FIG. 7, lane 2).

The details concerning the conditions under which the constructions of DNA recombinants were obtained and the methods used for appreciating the results asserted hereabove, inasmuch as they are not ascertainable from the previous discussion will be recalled hereafter.

MATERIALS AND METHODS

Strains and plasmids

E. coli DH1 was used for in vitro transformation. Agrobacterium C58CIRif was the receptor strain in all bacterial conjugations. The conjugation followed the protocol described by Van Haute et al. (1983) and ZAMBRYSKI et al. (1984).

DNA techniques

Restriction endonucleases and other DNA modifying enzymes were used as recommended by the manufacturers. Other techniques were used as described by MANIATIS et al. (1982).

Nopaline assay

The presence or synthesis of nopaline due to expression of the nos gene in transformed calli and regenerating shoots from these calli was monitored according to OTTEN (1982).

Plant transformation

Small axenically growing plants were kept in ½ M+S medium (MURASHIGE and SKOOG, 1962) in jars and were inoculated after decapitation with Agrobacterium strains as described (ZAMBRYSKI et al., 1984). Wound calli were removed and put on medium containing 0.2 mg/l benzaminopurine and 0.6 mg/l indolacetic acid and 0.5 mg/ml cefotaxime (HOECHST). After ca. 4 weeks the callus material was transferred to hormone free medium and emerging shoots were tested for nopaline production. Nopaline synthase positive shoots were propagated and tested on 100 to 500 ug/ml kanamycin. Teratoma shoots which grew on concentrations of 100 ug/ml or higher were used for analysis. Protoplast were kept in coculture with Agrobacteria according to MARTON et al. (1979) with modifications described by HAIN et al. (1985).

Analysis of DNA and RNA

DNA was isolated according to BEDBROOK (1981) from preparations of nuclei. The DNA was digested with restriction endonucleases (10–30 ug/lane, overnight digestion with a 3-fold excess of enzymes), separated on agarose gels according to size and transferred to nitrocellulose filters (THOMAS, 1983). Hybridization with radioactive probes was performed in 50% formamide, 4 times SSC, 10 times Denhardt's solution, 0.2 SDS and 0.1 mg/ml calf thymus DNA at 50° C. for 48 hours (BOHNERT et al., 1982). The filters were washed twice for 15 minutes each in 50% formamide, 4 times SSC at the hybridization temperature, followed by washing in 50% formamide, 3 times SSC at room temperature (1–4 hours) and 2 times SSC at room temperature (1 hour). Dot blot hybridizations were performed according to THOMAS (1983) with DNA amounts covering a range equivalent from 1000 to 0.1 gene copies per sample. Hybridization was as described above. RNA was isolated according to CHIRGWIN et al. (1979), and separated into poly (A)+ and poly (A)–RNA by passage over oligo d(T)-cellulose (Collaborative Research, type III) following the procedure of AVIV and LEDER (1972). RNAs were separated according to size in 1% agarose gels containing 5 mM methylmercury hydroxide (BAILEY and DAVIDSON, 1976). Hybridizations with $^{32}$P-labelled, nick-translated probes were carried out as described (BOHNERT et al., 1982); between 2 and $3 \times 10^6$ cpm/lane were used.

Neomycin phosphotransferase activity assay

The assay was adapted for plant extracts from a procedure worked out for bacterial and animal cell lysates (REISS et al., 1984a). Between 20 and 100 mg of tissue from transformed plants was crushed in 0.1 ml buffer (10% glycerol, 5% ∞-mercaptoethanol, 62.5 mM tris/HCl, pH 6.8, 50 ug/ml bromophenol blue and 0.1% SDS). Several protease inhibitors were used in an attempt to inhibit specific and unspecific proteases. Aprotinin (Trade name Trasylol) was used at a final concentration of 100 ug/ml in water. p-hydroxy-mercuri-benzoate (PHMB) was used at a concentration of 1 mM, ϵ-amino-n-caproic-acid and 1–10-phenantroline were added to a final concentration of 5 mM. Protease inhibitors were used according to Gray (1982). Cristalline phenylmethylsulfonylfluoride (PMSF) was added immediately before use at a concentration of 100 ug/ml. The cleared homogenate (5 min., 13,000 rpm, Eppendorf centrifuge) was loaded onto 10% non-denaturing polyacrylamide gels (Laemmli, 1970; without SDS). After electrophoresis the buffer in the gel was exchanged against 67 mM Tris/maleate, 42 mM MgCl2, 400 mM NH4Cl, pH 7.1, and the acrylamide gel was covered by an agarose gel (1%) containing kanamycin-sulfate (1 mg/ml) and $\gamma^{32}$P-ATP (5 uCi/um pf a specific activity of 2000–3000 Ci/mMol in the same buffer as the polyacrylamide gel. The gel-sandwich was covered by Whatman P81 paper, Whatman 3MM paper, and paper towels. After 3 hours the P81 paper was incubated for 30 minutes in a solution containing 1% SDS and 1 mg/ml proteinase K in water at 60° C. and subsequently washed several times in 10 mM phosphate buffer (pH 7.5) at 80° C., dried and exposed to Kodak XR5 film for up to 48 hours. The principle of this method is the binding of kanamycin to the phosphorylated DEAE paper by which the positions in the gel are revealed where a kanamycin phosphorylating activity migrated. The additional proteinase treatment suppresses signals of plant activities which after phosphorylation bind to P81 paper but do not phosphorylate kanamycin.

Isolation of chloroplasts

Chloroplasts were isolated from 1–2 g of leaves of transformed plants. Structurally intact chloroplats were collected from Percoll (Pharmacia) gradients (Ortiz et al., 1980). The washed chloroplasts were concentrated by centrifugation, lysed and than used for the in situ demonstration of NPTII activity as described above. Trypsinisation of chloroplasts was performed according to BARTLETT et al. (1982).

CONSTRUCTIONAL DETAILS AND METHOD EMBODIMENTS IN RELATION TO THE DRAWINGS

1) Construction of the chimaeric rbcS-npt-II genes pSNIP and pSNIF (FIG. 1A).

A BamHI-SalI fragment from pKM109/9 REISS et al., 1984b) containing the entire coding region from a modified nptII gene from Tn5 (BECK et al., 1982) was inserted in plasmid pPSR6 Δ-RV next to a 950 bp DNA fragment (EcoRI-EcoRV) containing the promotor region and the 5'-end of the rbcS gene resulting in plasmid I-22. In this plasmid the HindIII-BamHI fragment was replaced by a HindIII-Sau3A fragment (53 bp) from the original rbcS clone (pPSR6) to form the plasmid II-4 containing the fusion gene. The pBR derived region in II-4 was exchanged against an EcoRI-SalI fragment from pGV710 in order to introduce streptomycin and spectinomycin resistance to be used as a marker to select for cointegration of this final plasmid (pSNIP (10.4 kbp)) with the Ti-plasmid in Agrobacterium. Plasmid pSNIF (12.3 kbp) was constructed by replacement of the SmaI-SalI fragment of pSNIP with an PvuII-XhoI fragment from the octopine synthase gene from plasmid pAGV40 (HERRERA-ESTRELLA et al. 1983; DE GREVE et al., 1983) harboring the polyadenylation site of that gene next to a BamHI restriction site of that gene next to a BamHI restriction site.

Figures 1B, 8B:
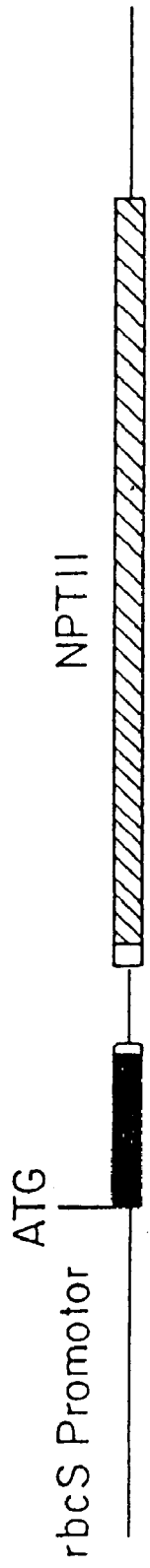
FIG. 1B represents the structure of the characteristic portion of the chimaeric gene according to this invention and included in the abovesaid recombinant DNAs.
FIG. 8B represents the amino acid sequences encoded by a portion of a chimaeric gene diagrammatically shown in FIG. 8A particularly at the junction of the DNA sequence coding for the selected transit peptide of a gene encoding the amino terminus of the bacterial neomycine phosphotransferate II (NPT(II) used as a model of protein of bacterial origin transportable into the chloroplasts.

2) Structure of the rbcS-npt-II chimaeric gene (FIG. 1B).

The black bar represents the transit-peptide sequence with the first ATG, the white area (two codons in exon 1 and 22 codons in exon 2) is interrupted by the first intron and represents the mature rbcS sequence. The hatched part represents the nptII sequence.

Figure 2:
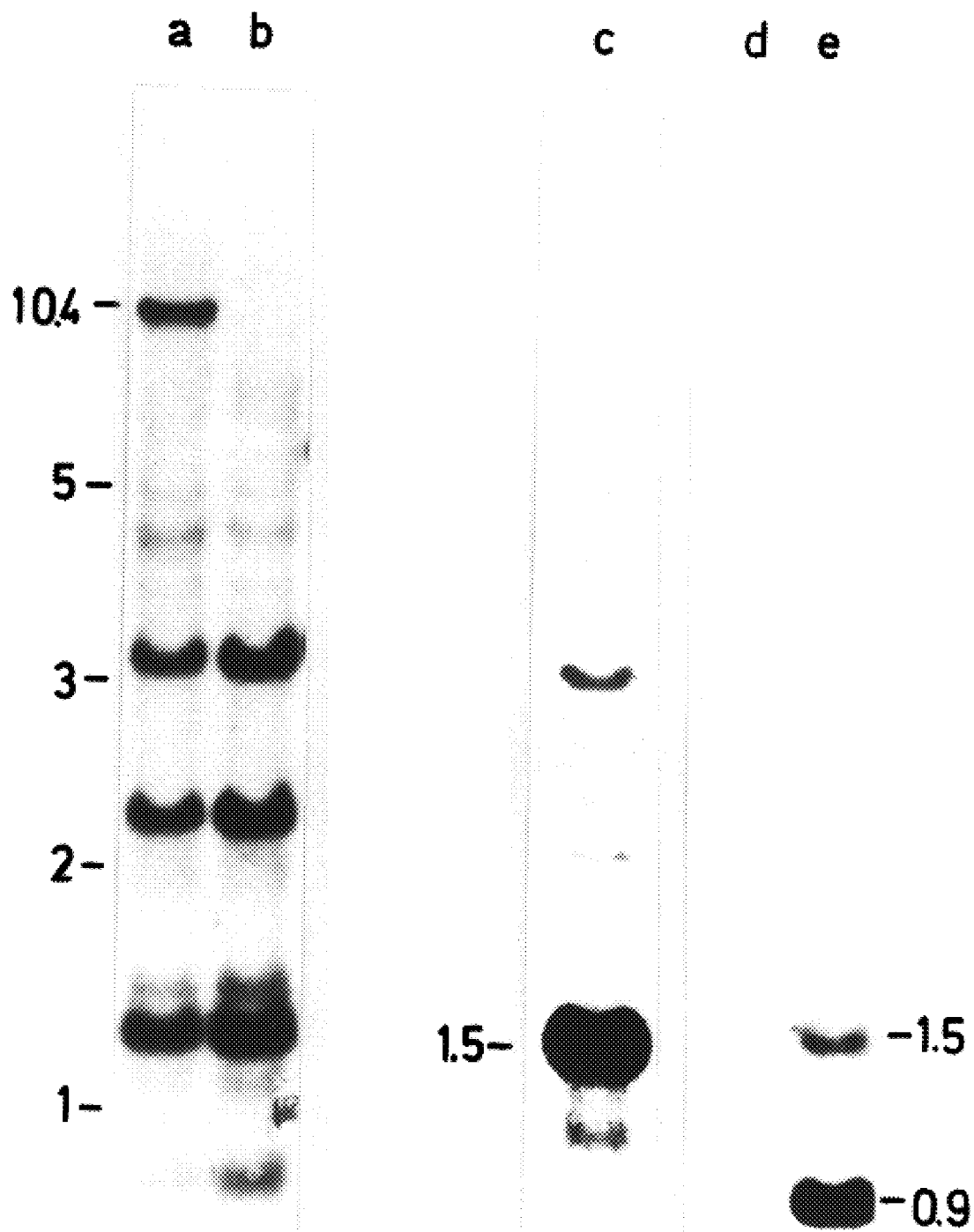
FIG. 2 shows the results obtained in Southern hybridization experiments with recombinant DNAs according to the invention, in relation to the detection of the incorporation of the abovesaid chimaeric gene in the genome of plant cells.

3) Southern hybridization experiments (FIG. 2).

Hybridization of different probes to nuclear DNA from transformed (pGV3851::pSNIP) (a, c and e) and untransformed (b and d) tobacco. In Southern hybridization experiments (Southern, 1975) lane a and b resolve bands of different size resembling the small subunit gene family when a 661 bp EcoRV-AvaIII DNA fragment from the genomic small subunit clone was used as probe (Cashmore, 1983). An additional band of 10.4 kbp reveals the chimaeric gene fragment in lane a. In lanes c, d and e DNA was digested with PstI and EcoRI and either the promoter region of the small subunit gene (972 bp EcoRI/HindIII fragment) (lane c and d) or the coding region of the nptII gene (1000 bp BamHI/SmaI fragment from plasmid pKM109/9) were used as probes. In lane c a strong signal is detected from untransformed material (lane d). Weak signals in lane c are most likely due to crosshybridization of endogenous rbcS sequences or incomplete digestion of the DNA. In lane e a band of 0.9 kbp lights up the internal PstI fragment of the nptII gene and the weaker band shows again the 1.5 kbp fragment seen in lane c, due to a small overlap between the probe and the promotor region of the chimaera.

Figure 3:
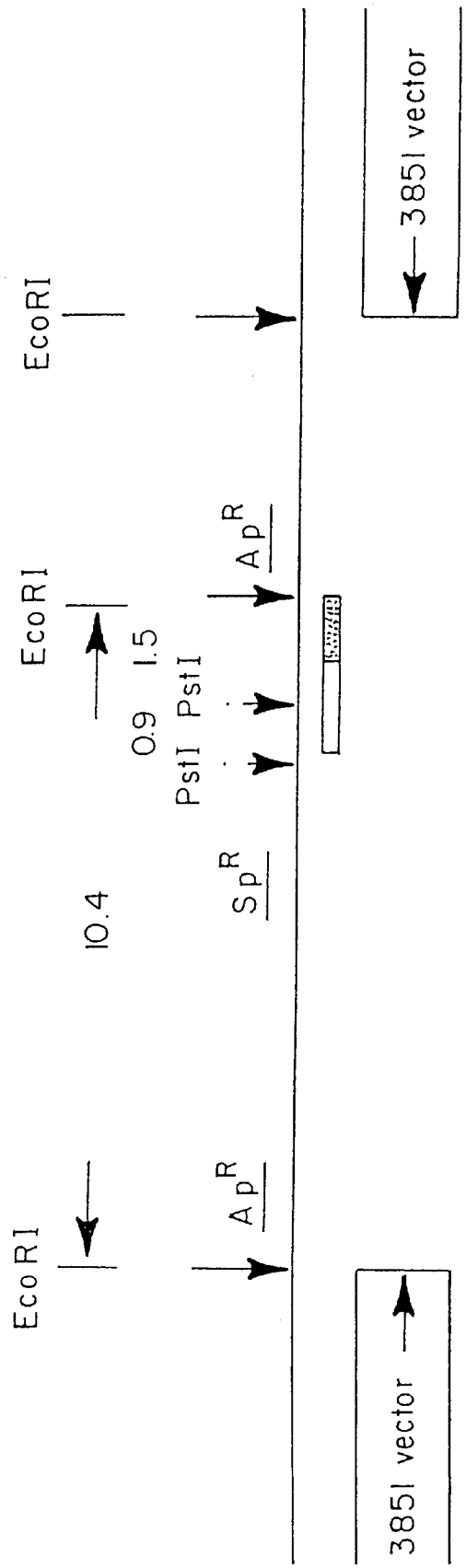
FIG. 3 is a schematic representation of the organization of the gene fusion and the plant-vector sequences of the vector of FIG. 1A, as modified by said chimaeric gene.

4) Schematic representation of the organization of the fusion and the flanking vector sequences (FIG. 3).

Sizes are indicated by kbp. the chimaeric rbcS-nptII coding region is indicated by an open bar, the 5'-flanking sequence by a closed bar. EcoRI and PstI indicate restriction endonuclease sites. SpR and ApR represent antibiotic resistance markers against spectinomycin and ampicillin. Numbers indicate the size of fragments obtained in the Southern experiments (FIG. 2). The DNA fragments between the gene fusion and the right part of the T-DNA represent the pBR322 sequences present in the vector pGV3851.

5) Transcriptional activity of rbcS promotor (FIG. 4).

RNA was separated in denaturing 1% agarose gels and transferred to nitrocellulose filters which were probed with different parts of the construction. The coding region of the nptII gene (BamHI-SmaI fragment from pKM109/9) was used as a probe. Lane 1: RNAs from light grown teratoma shoots. Lane 2: RNAs from plant material kept in darkness for four days after a day/night rhythm of twelve hours. Lane 3: RNAs from plant leaves transformed with pGV3850. Lane 4: RNAs from wild type Wisconsin 38. Weak signals in the latter are probably due to contaminating material in the probe which hybridizes to mRNA promotor active in the T-DNA or near the position of insertion in the plant chromosome. Numbers on the left indicate size in nucleotides, numbers on the right refer to the Svedberg values of RNA markers.

6) Comparison of light dependence of rbcS and rbcL promotors (FIG. 5A).

Poly (A)+ RNA from teratoma shoots grown in a daily rhythm of 12 hours light/dark (L) and material kept subsequently for four days in the dark (D) were hybridized to an nptII specific probe (see FIG. 4) and to a rbcS specific probe (see FIG. 2). The endogenous rbcS transcripts are observed at the position of 850 nucleotides. Poly(A)-RNA was analysed with the same technique probed with a 1750 bp fragment from a rbcL gene (ZURAWSKI et al., 1981). Numbers on the left refer to Svedberg values of RNA markers or to the size of the mRNA (right).

7) Dot Blot Hybridization to RNA From Transformed (pGV3851::pSNIP) Plant Material (FIG. 5B)

L indicates light grown material in 12 hour light/dark cycle. D indicates subsequent growth in the dark for four days. Single dots where cut out and radio-activity measured.

8) Demonstration of Transport of TP-SS-NPTII Precursor in Chloroplasts of Tobacco Plants Containing the pGV3850::pSNIF Construct (FIG. 6A)

The results obtained in each lane are commented hereafter:

Lane 1: extracts from E. coli pGLT neo1 expressing a TP-NPTII protein (VAN DEN BROECK et al., Nature in press) in E. coli pKM2 containing the TN5 encoded NPTII enzyme.

Lane 2: Neomycinphosphotransferase activity in chloroplasts purified from leaves of tobacco plants containing the chimaeric tp-ss-nptII gene.

Lane 3: Crude extract from leaves of a control SR1 tobacco plant.

Lane 4: Crude extract from leaves of tobacco plants containing the chimaeric tp-ss-nptII gene. The P.K. band is presumed to be due to a cytoplasmic self-phosphorylating protein and C.P.K. is presumed to be due to a chloroplast self-phosphorylating protein.

Figure 6B:
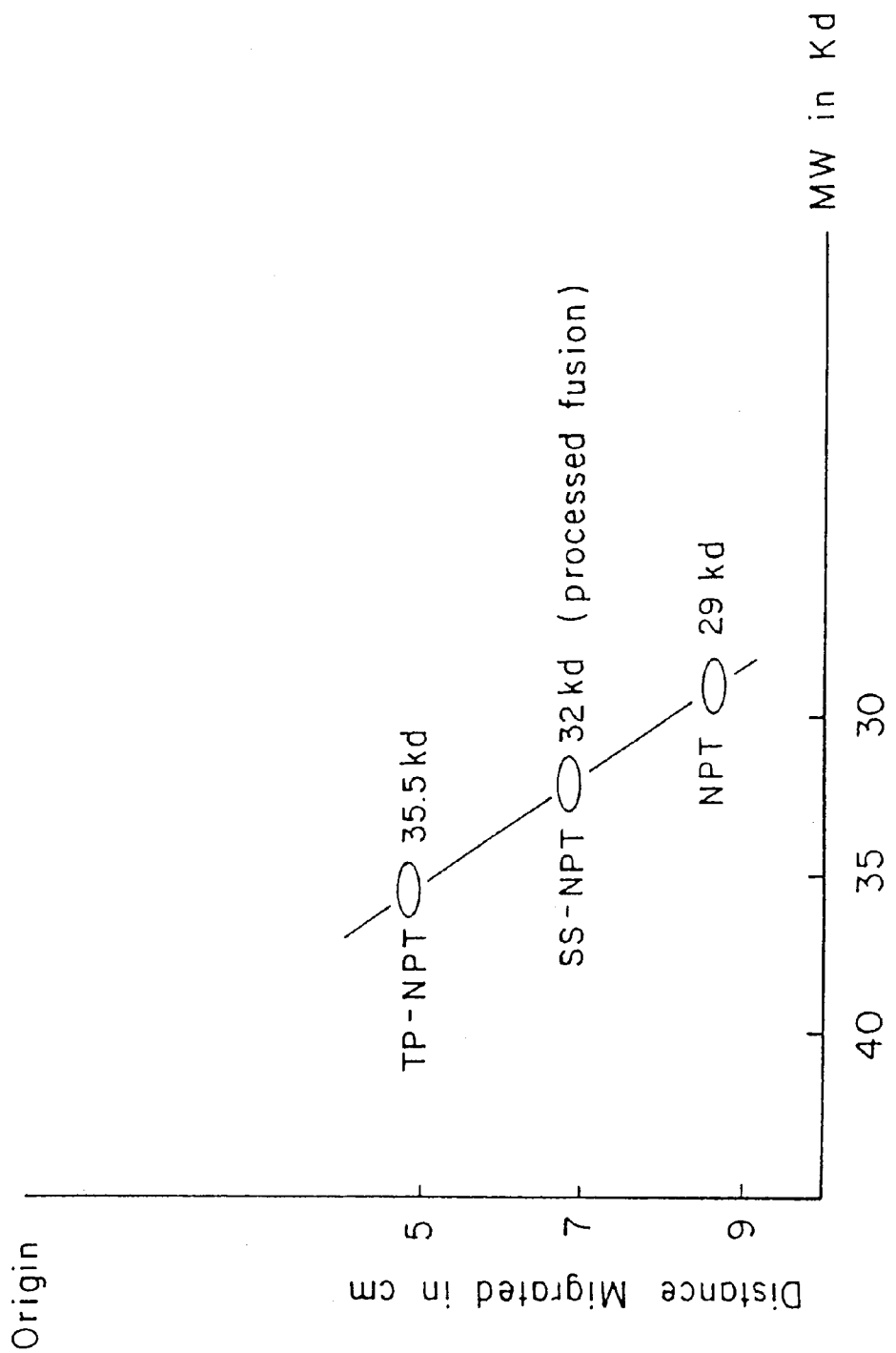
FIG. 6B is a graphic display of the relative mobility of the different activities of the gene-produce detected in FIG. 6A.
Figure 7:
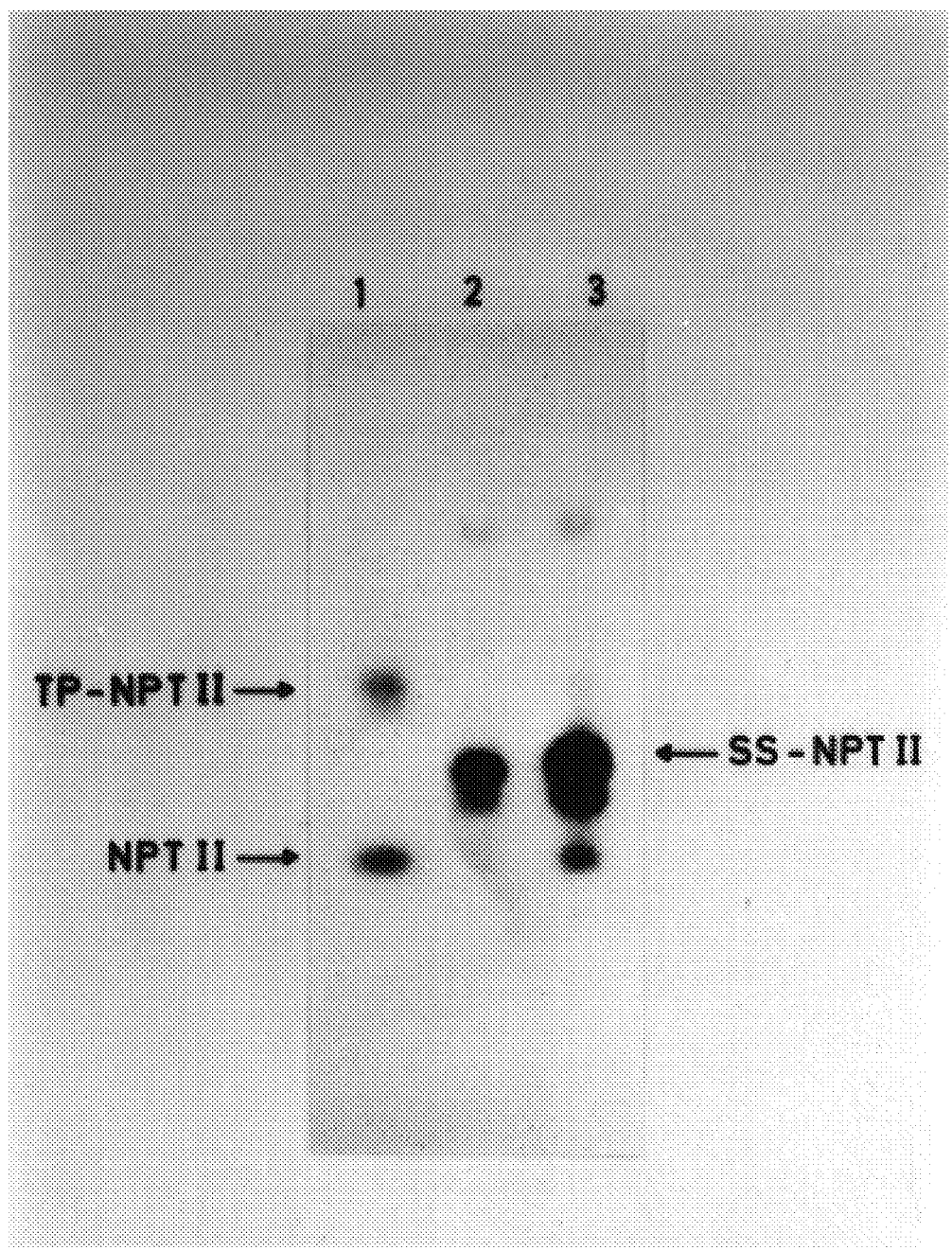
FIG. 7 illustrates results obtained in assays (to show the light-dependent expression of the fusion protein encoded by the chimaric gene)

9) Graphic Display of the Relative Mobility of the Different NPTII Activities Detected in FIG. 6A (FIG. 6B)

As described hereabove it is legitimate to make the assumption that these proteins are separated according to molecular weight on these native gels because of their very similar polarity index (CAPALDI and VANDERKOOI; 1972).

10) Light Dependant Expression of the SS-NPTII Fusion Protein (FIG. 7)

Lane 1: Idem as for FIG. 6A.

Lane 2: Idem as for FIG. 6A lane 4 except for the fact that the plants were kept in complete darkness for 96 hours before extraction. Lane 3: Idem as for FIG. 6A. lane 4.

The results obtained demonstrate that the use of Agrobacterium vectors to transfer and express genes in plant cells (amply documented by CAPLAN et al., 1983; ZAMBRYSKI et al., 1983; 1984; HERRERA-ESTRELLA et al., 1983; 1984) can be extended to target a foreign protein for a specific cell compartment, namely the chloroplast. The results further demonstrate (i) that the gene fusion is integrated in the nuclear DNA of tobacco without rearrangement of the DNA that the transcription of this chimaeric gene (which contained a light inducible promoter sequence) is regulated by light.

It is important to note that the induced transcription of this introduced gene is as efficient as that of the endogenous small subunit gene(s) and rather more efficient than previously observed in tobacco with another chimaeric gene using the same pea small subunit promoter (HERRERA-ESTRELLA et al., 1984). Possibly the higher level of induced steady state mRNA in these tissues is due to improved mRNA stability. The presence of one intron in the transcript derived from this transit peptide small subunit neomycin phosphotransferase chimaeric gene (tp-ss-nptII) and the absence of any intron in the construction described by HERRERA-ESTRELLA et al., (1984), might explain an increased stability of this RNA (Hamer and Leder, 1978). Our observations also demonstrate that the pea small subunit promoter can be active in leaves of normal tobacco plants. This is in contrast to previous observations in several laboratories which indicated that the pea small subunit promoter while active in tobacco tissue cultures and teratomas, was inactive in leaves of normal plants. Possibly a position effect is involved in this phenomenon, the chimaeric tp-ss-nptII gene in (pGV3851::pSNIP) did not contain a polyadenylation or a transcription termination signal, which probably explains the observed very large transcripts. It will be shown in Example II that the provision of a suitable polyadenylation or a transcription termination signal at the appropriate location after the nptII gene results in the production of transcripts having substantially the same lengths as the transcripts of the nptII in its natural environment.

The data obtained hereabove demonstrate that the chimaeric tp-ss-nptII gene, which upon expression yields a fusion protein with a transit peptide and the conserved amino acid sequence flanking the processing site, is indeed translocated to the chloroplasts and is processed to yield a fusion protein located in the stroma, consisting of the $NH_2$-terminal end of the small subunit protein and an active NPTII protein. This SS-NPTII fusion protein migrates in the gel NPTII-assay with an electrophoretic mobility which is intermediate between the TP-NPTII (35.5 kd) and that of the original NPTII activity (29 kd). This mobility is in very good agreement with the molecular weight (32,298) of the SS-NPTII fusion protein. The results obtained indicate that this fusion protein, which confers kanamycin resistance to the transformed tobacco plants, is located within the chloroplasts and might leak out when the chloroplasts are broken.

However, the results obtained with the construction described in Example II hereafter demonstrate that the NPTII component of a precursor protein which contains only the transit peptide sequence immediately fused to the NPTII protein and thus missing part of the conserved aminoacid sequence flanking the processing site, is equally translocated across the chloroplast envelope and apparently properly processed. The latter results indicate that the transit peptide sequence alone is sufficient to both transport and process precursor proteins into chloroplasts.

EXAMPLE II

In this example a chimaeric gene encoding a fusion protein consisting of the transit peptide of the precursor to the small subunit of RuBP carboxylase from pea[44] directly linked to the amino-terminus of NPT(II) was constructed.

In other words the bacterial enzyme into a novel "precursor" polypeptide was tested for its ability to be post-translationally imported and processed by chloroplasts both under in vivo and in vitro conditions.

General Outline of the Plasmids Construction

Figure 8A:
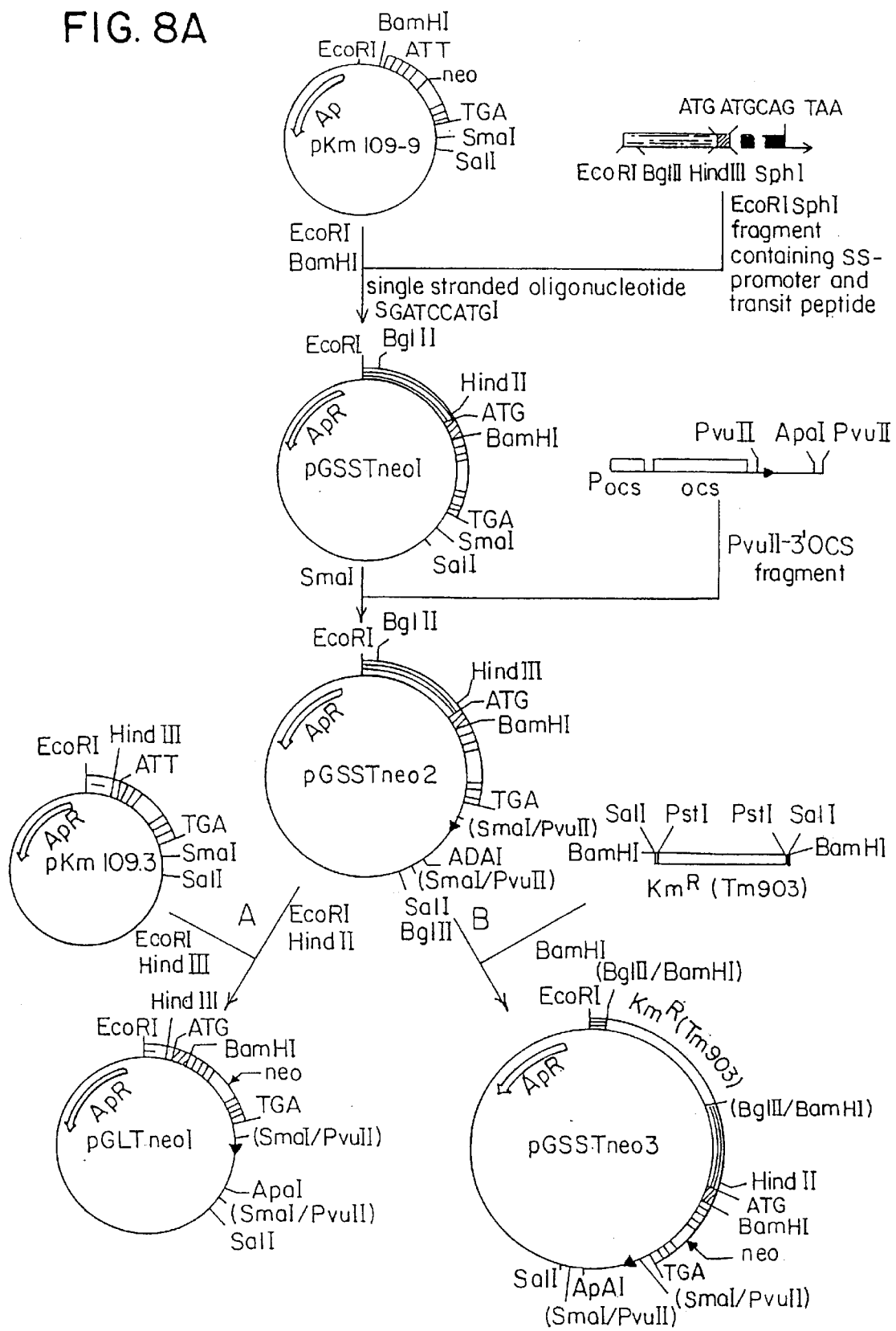
FIG. 8A diagrammatically represents successive steps of the construction of preferred recombinant DNAs according to a second preferred embodiment of the invention, as well as of other recombinant DNAs for study purposes.

Two plasmids have been constructed which contain chimaeric genes encoding TP-NPT(II) (FIG. 8A). In the first plasmid, pGSSTneo3, the coding sequence for TP-NPT(II) is under control of the pea ss3.6 promoter which directs expression of chimaeric genes in plant cells[42,45]. This construction has been used to study the fate of the fusion protein in vivo in transformed tobacco cells. Another plasmid, pGLTneo1, was constructed to direct the synthesis of TP-NPT(II) in *E. coli* under control of the lacUV5 promoter[45] in order to obtain sufficient quantities of the fusion protein for use in in vitro reconstitution experiments with isolated chloroplasts. The fusion protein encoded in both plasmids consists of the 57 amino acid transit peptide and the first methionine of the mature small sub-unit polypeptide encoded by the pea ss3.6 gene[44], a 7-aminoacid linker fragment, and the NPT(II) devoid of the first methionine[45] (263 aminoacids). The amino acid sequences in the authentic small sub-unit precursor encoded by ss3.6 and the fusion protein are compared in FIG. 9 lane 2. It can be seen that the Cys/Mot cleavage site of the precursor to the small sub-unit is left intact in the TP-NPT(II) fusion protein.

To study the fate of the TP-NPT(II) fusion protein in vivo, it was necessary to first obtain transformed plant cells expressing the tp-npt(II) gene product.

The tp-npt(II) gene of pGSSTneo3 was brought into the genome of plant cells by means of the vector pGV3851, a derivative of the Agrobacterium Ti-plasmid pTiC58[48]. The plasmid pGV3851 contains a deletion which removes several of the T-DNA-encoded transcripts, including those involved in auxin production, but retains the gene involved in cytokinin synthesis. The result of this modification is that Agrobacterium harbouring pGV3851 induces shoot-forming tumours. In pGV3851, the deleted portion of the T-DNA has been replaced by pBR322. pGSSTneo3 was inserted into the T-DNA of pGV3851 by recombination through the pBR322 homology[49].

Figure 9:
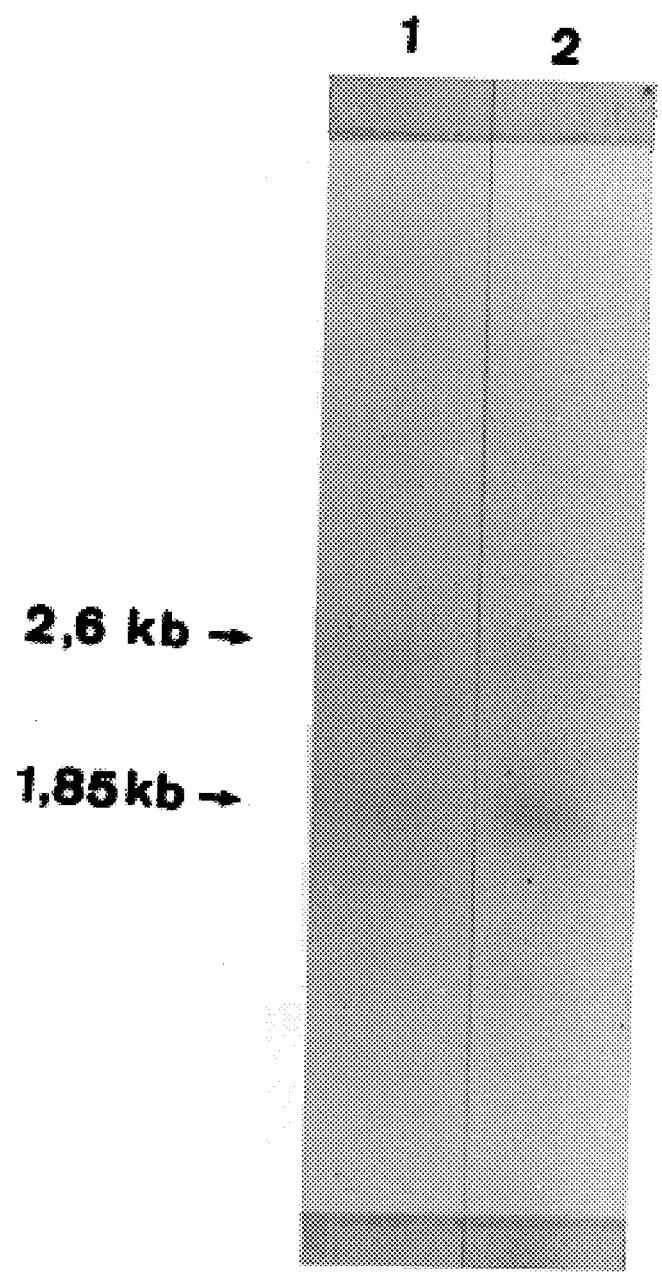
FIG. 9 shows the results of Southern hybridization analysis of Agrobacterium and plant DNA as described in Example II.

The T-DNA of several Agrobacterium exconjugants obtained on kanamycin-containing plates was examined by Southern hybridization analysis[50] to confirm that the proper cointegration between pGSSTneo3 and the T-DNA of pGV3851 had occurred. The results obtained for one of these pGV3851::pGSSTneo3 exconjugants is shown in FIG. 9, lane 1.

Stems of sterile tobacco seedlings were inoculated with this strain after wounding with a needle below the first internode. After 2–3 weeks, green, shoot-forming tumours appeared. Axenic tissue was obtained by growing the transformed tissue in vitro on Murashige and Skoog (MS) medium[52] containing 500 µg/ml of cefotaximum, an antibiotic to which ampicillin-resistant agrobacteria are sensitive. During propagation of the tissue, the sucrose concentration of the MS medium was reduced from 3% to 1% to improve greening. The green tissues were able to grow on medium containing 200 μg/ml of kanamycin, indicating that the tp-npt(II) gene was present and functionally expressed. The presence of the tp-npt(II) gene was confirmed by Southern hybridization analysis[50] of genomic DNA obtained from the transformed callus tissue (FIG. 8B).

A parallel series of cointegration and transformation experiments (data not shown) provided tobacco tumours containing a second chimaeric gene, nos-npt(II)[ref 40] coding for the unaltered NPT(II) protein under control of the promoter from the nopaline synthase gene[35,43]. This allowed the study the fate of NPT(II) itself in transformed cells.

Fate of the tp-npt(II) Gene Product in Plant Cells

Since the TP-NPT(II) fusion protein is not a normal component of plant cells, it was of interest to determine the final location of the fusion protein in transformed cells. Specifically, we wished to know whether the transit peptide alone is capable of directing the uptake and processing of the TP-NPT(II) fusion protein by chloroplasts in vivo. Therefore, the following series of experiments were performed to determine the fate of both TP-NPT(II) fusion protein and unaltered NPT(II) in transformed tobacco cells.

Figure 10:
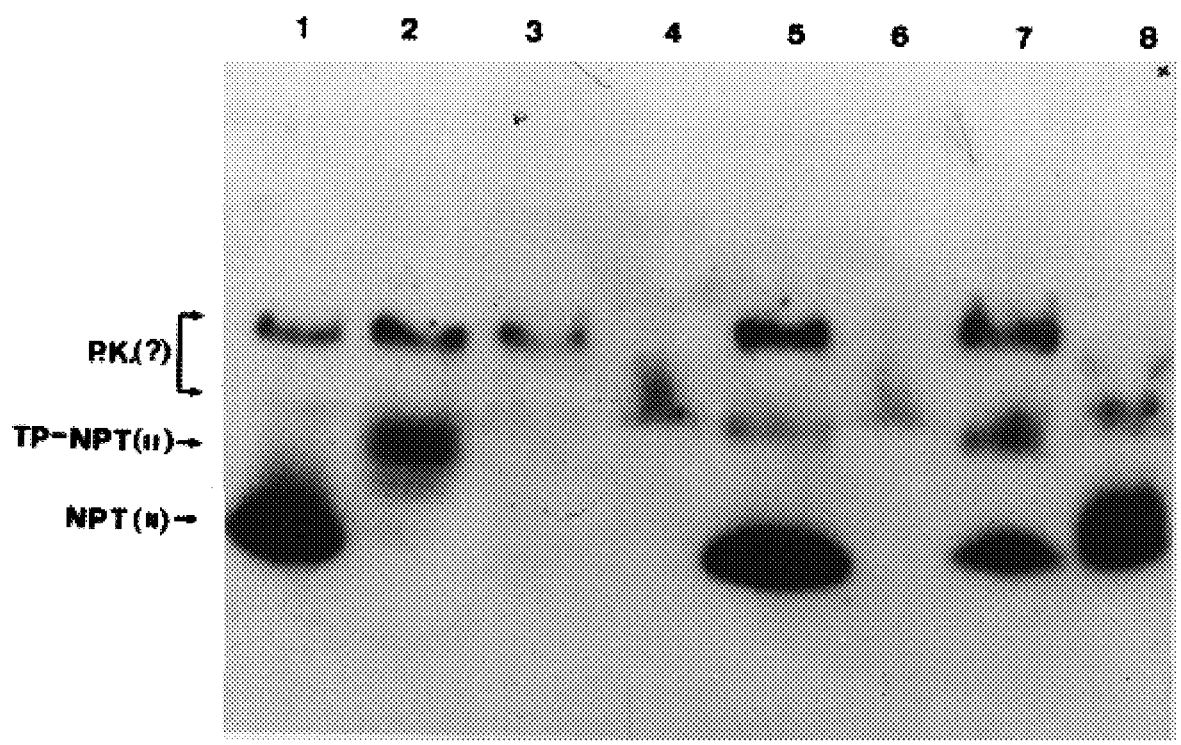
FIG. 10 is an autoradiogram showing the localization of NPT(II) activity in chloroplasts of tobacco callus tissue as described in Example II.

The presence of NPT(II) or active NPT(II) fusion proteins in a given extract can be determined using an in situ enzymatic assay for phosphotransferase activity after gel electrophoresis (FIG. 10). The positions of the original NPT(II) and the TP-NPT(II) fusion protein were determined by assaying extracts of E. coli harbouring either pBR322::Tn5 or pGLTneo1, prepared as described[47]. As shown (lane 3, FIG. 10), the enzymatic assay on extracts of plant tissue that does not contain the NPT(II) coding sequence in its genome reveals two bands of phosphotransferase or kinase activity (these are noted by P.K., plant kinase). These bands do not represent NPT(II) activity since they can also be observed when no kanamycin is included as substrate in the enzymatic reaction (data not shown). The faster migrating band is also found with chloroplast preparations from the same tissue (lane 4, FIG. 10). When a bacterial extract containing the TP-NPT(II) fusion protein encoded by pGLTneo1 is mixed with plant extract, a new major band of NPT activity appears (lane 2, FIG. 10). This band migrates more slowly than NPT(II) encoded by Tn5 (lane 1, FIG. 10), and probaby corresponds to the bona fide TP-NPT(II). The change in mobility is due to a change in both molecular weight and charge as a result of the addition of the transit peptide. In lane 2 (FIG. 10), also minor bands with higher mobility can be observed. These likely correspond either to degradation products of the fusion polypeptide, or to smaller polypeptides translated from an internal ATG of the TP-NPT(II) coding sequence.

Crude extracts obtained from transformed tissue containing a nos-npt(II) chimaeric gene contain NPT(II) activity (lane 5, FIG. 10). However, intact chloroplasts isolated from the same tissue do not have detectable NPT(II) activity associated with them (lane 5, FIG. 10). This observation suggests that the product of this chimaeric gene lacks the information necessary to mediate its translocation into chloroplasts. Crude extracts from tissue containing the tp-npt(II) chimaeric gene also contain considerable NPT(II) activity (lane 7, FIG. 10). When intact chloroplasts are isolated from this tissue, considerable levels of NPT(II) activity are found to be associated with them (lane 8, FIG. 11). Moreover, the one neomycin phosphorylating protein observed in both the crude extract and the isolated chloroplats, migrates with the same mobility as the Tn5 authentic protein, and differs from the NPT(II) fusion protein from E. coli harbouring the tp-npt(II) chimaeric gene (see also FIG. 11, lanes 1, 2, 3). Even after longer exposure of the auto-radiogram there was no indication of the presence of this NPT(II) fusion protein. These observations show that the NPT(II) activity is concentrated in the chloroplast fraction, and that the TP-NPT(II) fusion protein is cleaved very efficiently close to the fusion site, removing the transit peptide.

Since the mature SS polypeptide is part of a soluble protein present in the stroma, it was of interest to determine whether the NPT(II) activity associated with the isolated chloroplast fraction is also sequestered in the same suborganellar compartment. Therefore, chloroplasts from pGV3851::pGSSTneo3-transformed tissue were lysed by resuspension in a hypo-osmotic buffer, and fractionated into stromal and membrane fractions. The membrane fraction was further washed to eliminate stromal contamination. Aliquots from these fractions were then subjected to electrophoresis on non-denaturing gels and assayed in situ for NPT(II) activity. The results of this analysis (FIG. 11) clearly demonstrate that all of the enzyme activity associated with the chloroplast fraction isolated from transformed tissue is located in the stromal (lane 3, FIG. 11) rather than membrane (lane 4, FIG. 11) fraction of the plastids. To ensure that these findings represent uptake of the fusion protein by the chloroplasts and not non-specific binding to the plastid envelope and release during organelle fractionation, aliquots of isolated chloroplasts were subject to protease treatment[53]. Equal amounts of chloroplasts from protease-treated and non-treated preparations were then fractionated as described above, and stromal fractions assayed for NPT(II) activity. A large percentage of the NPT(II) activity present in non-treated chloroplasts (lane 3, FIG. 12) remains present in protease-treated chloroplasts (lane 4, FIG. 12) until these chloroplasts are broken (lane 2, FIG. 12). the slight decrease in activity observed is likely the result of losses from plastid lysis rather than the lack of sequestering of the processed fusion protein within the chloroplast.

These results, clearly demonstrate that the TP-NPT(II) fusion protein is targeted to the chloroplast, translocated into the stroma, and processed in a fashion similar to that of the small subunit polypeptide.

In vitro Uptake and Processing of the Fusion Protein by Isolated Chloroplasts

As an alternative approach to determine whether the transit peptide alone is sufficient to direct post-translational uptake of proteins other than the mature small subunit polypeptide into chloroplasts and to test whether chloroplasts can recognize and proteolytically remove the transit peptide of a fusion protein, a series of in vitro reconstitution experiments were carried out with isolated intact chloroplasts. The in vitro approach has previously been shown to be useful in the analysis of chloroplast translocation processes[6,10-17]. Here, we have adapted this method for use with fusion proteins produced by E. coli.

Bacterial extracts containing the TP-NPT(II) fusion protein were prepared by sonication of exponentially growing liquid cultures of Escherichia coli harbouring pGLTneo1. Aliquots of the TP-NPT(II) containing cleared bacterial extracts were incubated for 1 hour with chloroplasts isolated from pea leaves[53]. Following incubation, the chloroplasts were reisolated form the incubation mix and washed several times an isosmotic buffer until no TP-NPT(II) activity was detected in the supernatant.

This preparation was used to determine whether there was NPT(II) activity associated with the stroma or membrane fraction of these chloroplasts. Lanes 1 and 2 or FIG. 6 show respectively the position of NPT(II) and TP-NPT(II) present in bacterial extracts. Lane 3 (FIG. 6) shows that prior to incubation with E. coli extracts containing TP-NPT(II), the stroma of chloroplasts isolated from pea does not contain any phosphotransferase or kinase activity comigrating with either the TP-NPT(II) fusion polypeptide or authentic NPT (II). However, as observed earlier in tobacco, our assay conditions reveal an endogenous kinase activity (P.K.) associated with chloroplasts. After incubating these chloroplasts with bacterial extracts containing TP-NPT(II), the stromal fraction obtained from the isolated organelles contains a considerable level of NPT(II) activity (lane 4, FIG. 6), whereas the membrane fractions does not (lane 6, FIG. 6). This NPT(II) activity migrates like the original bacterial enzyme, which indicates processing. To confirm that the NPT(II) activity observed in the stromal fraction of chloroplasts incubated in the presence of the TP-NPT(II) fusion protein was the result of uptake and not the result of liberation during the fractionation procedure of protein bound to the chloroplast envelope, chloroplasts were reisolated from the uptake incubation mixture, washed and subjected to limited proteolysis[53]. Following repurification, protease-treated chloroplasts were fractionated as above, and the NPT(II) activity was determined in both the stromal and membrane fractions. Most of the stromal NPT(II) activity appears to be protected against protease digestion since the amount of activity recovered (lane 55, FIG. 6) is similar to that found in non-treated chloroplasts (lane 4, FIG. 6). The membrane fraction of protease-treated chloroplasts was completely free of activity (lane 7, FIG. 6). Similar results on in vitro uptake of the TP-NPT(II) fusion protein have been obtained using intact chloroplasts isolated from young expanding tobacco leaves (data not shown).

These results demonstrate that the transit peptide of the precursor to the small subunit of ribulose-1,5-bisphosphate is capable of mediating the uptake of polypeptides other than the mature small subunit by chloroplasts under in vitro assay conditions. That uptake of the NPT(II) protein by chloroplasts in vitro does not occur in the absence of the transit peptide (data not shown) is consistent with our in vivo observation that chloroplasts prepared from callus tissue transformed with nos-npt(II) do not contain activity. These observations further confirm the requirement for the transit peptide in the translocation process.

Unlike previous in vitro uptake studies[6, 11-17] which relied on the use of wheat germ extracts for the synthesis of precursor, polypeptides, we have used an E. coli expression system for the preparation of our fusion protein. Since translocation of the fusion protein proceeds in this in vitro uptake system, this may be taken as an evidence for the lack of a requirement for additional cytoplasmic factors in the translocation mechanism. However, in contrast to translocation studies with microsomal membranes[54], it is not practical to wash chloroplast preparations with high salt buffers. Consequently, we cannot completely eliminate the possibility that the translocation of chloroplast proteins requires additional cytoplasmic factors which may be tightly bound to our chloroplast preparations.

1-Detailed Description of the Construction of Plasmids Containing Chimaeric Genes Encoding the TP-NPT(II) Fusion Protein (FIG. 8A)

A 1-kb EcoRI-SphI restriction fragment from pPSR6, a pBR327 derivative containing the pea small subunit ss3.6 gene[44], was purified from a 1% agarose gel. This fragment, which contains the promoter region, nucleotide sequences encoding the transit peptide and first methionine codon of the mature small subunit polypeptide, was ligated into EcoRI/BamHI-cut pKm109/9 to replace the small EcoRI/BamHI fragment in front of the NPT(II)-coding region. The plasmid pKm109/9 is a pBR322 derivative containing the npt(II) gene of Tn5 devoid of its 5'-untranslated region and the first methionine codon[45]. To fuse the 3'-overhanging end of the SphI restriction site with the 5'-overhanging end of the BamHI restriction site, a single-stranded oligonucleotide 5' GATCCATG 3', complementary to both protruding ends, was synthesized and added to the ligation mix[55]. After fusion, the SphI site is abolished, but the BamHI site remains. The resulting plasmid, pGSSTneo1, was restricted with SmaI and a 700-bp PvuII fragment, containing the transcription termination and polyadenylation signal from the ocs gene[56], was ligated into the site to ensure proper 3' transcription termination and processing. The intermediate pGSSTneo2 plasmid was then used in two different cloning steps.

(A) A 1,400 bp BamHI fragment from pUC4K$^{ref.57}$ encoding the kanamycin resistance gene from Tn903 was isolated and cloned into the unique BglII restriction site of pGSSTneo2 yielding the plasmid pGSSTneo3. Kanamycin resistance is used as a marker to select for the cointegration of pGSSTneo3 with the Ti-plasmid in Agrobacterium.

(B) A 200 bp EcoRI/HindIII fragment from pKm109/3$^{ref.45}$ containing the lacUV5 promoter region, was exchanged for the small EcoRI/HindIII fragment of pGSSTneo2. This allows for the expression of the TP-NPT(II) fusion protein in E. coli. The resulting plasmid is referred to as pGLTneo1. Abbreviations: Ap$^R$, ampicillin resistance; Km$^R$, kanamycin resistance. Symbols: ———, pBR322 sequence; [[[neo▨▨▨, coding region for NPT(II); [→▨, lacUV5 promoter region; Δ, 3' end. Representation of the octopine synthase gene: [Pocs▨, promoter region; [ocs ▨ coding region. Representation of the gene for the small subunit of ribulose-1,5-bisphosphate carboxylase: [══════▨ , promoter and 5'-untranslated region; [//////▨, sequence encoding the transit peptide; [▨, exon; [▨, intron.

2-Partial Aminoacid Sequence Comparison of the TP-NPT (II) Fusion Protein and the Precursor to the Ribulose-1,5-bisphosphate Carboxylase Small Subunit Polypeptide (FIG. 8B)

Partial aminoacid sequences for the precursor to the small subunit polypeptide or ribulose-1,5-bisphosphate carboxylase encoded by the pea ss3.6 gene[44] (upper line) and the TP-NPT(II) fusion protein (lower line) are presented. The area near the processing site of the small subunit precursor and the fusion point for the TP-NPT(II) fusion protein are shown. The arrow indicates the protoolytic processing site defined for the small subunit precursor. The amino acid residues derived from the original NPT(II) protein are underlined. Amino acid residues are numbered above the sequences with the first methionine residue of the mature small subunit protein being taken as aminoacid number 1.

Met . . . Ser Asn Gly Gly Arg Val Lys Cys Met Gln Val Trp Pro Pro Ile Gly Lys Lys . . .

Met . . . Ser Asn Gly Gly Arg Val Lys Cys Met Asp Pro Ala Asn Leu Ala Trp Iso Glu

3) Incorporation of tp-npt(II) Gene Into the Genome of Plant Cells

To insert pGSSTneoIII in between the PGV3851 T-DNA borders, pGSSneoIII was first introduced into the E. coli strain Gj23 which harbours the helper plasmids R64drdII and Gj20. These last two plasmids provided the Tra and Mob functions required to mobilize pGSSTneo3 from *E. coli* to *Agrobacterium tumefaciens* (harbouring pGV3851). Thus, after conjugation between the corresponding *E. coli* and *A. tumefaciens* strains, Agrobacterium exconjugants the cointegrate between pGSSTneoIII and pGV3851 were selected on kanamycin containing plates.

The T-DNA of several kanamycin-resistant Agrobacterium exconjugants was examined by Southern hybridization analysis[50] to confirm that the proper cointegration between pGSSTneo3 and the T-DNA of pGV3851 had occured. The result obtained for one of these pGV3851::pGSSTneo3 exconjugants is shown in FIG. 3.

Reference is also made at the more detailed description of FIG. 10 which appears hereafter.

4) Southern Hybridization Analysis of Agrobacterium and Plant DNA (FIG. 9)

The autoradiogram above shows the results of Southern hybridization[50] analysis confirming the presence and the structure of the tp-npt(II) chimaeric gene in both cointegrate pGV3851::pGSSTneo3 DNA and in genomic DNA from transformed tobacco cells. Lane 1, total Agrobacterium DNA from pGV3851::pGSSTneo3; lane 2, plant genomic DNA from tobacco callus transformed with pGV3851::pGSSTneo3. In both lanes two fragments hybridize with the specific probe: one fragment of 2.6 kb representing the EcoRI/BamHI fragment of pGSSTneo3 containing the $Km^R$ gene of Tn903 and the SS promoter and transit peptide region; a second fragment of 1.85 kb representing the BamHI/SalI fragment of pGSSTneo3 that contains the coding region of NPT(II) and the OCS 3' end.

Total Agrobacterium DNA[58] and plant genomic DNA from transformed callus tissue[59] were prepared and restricted with EcoRI, BamHI, and SalI. Digest products were fractionated on a 1% agarose gel, transferred to nitrocellulose paper, and hybridized with a $^{32}$P-labelled probe specific for the promoter and the coding region of the TP-NPT(II) fusion protein (the probe was the smaller EcoRI/SalI fragment of pGSSTneo1; see FIG. 8A).

5) Localization of NPT(II) Activity in Chloroplasts Callus Tissue (FIG. 10)

The autoradiogram shows the presence and mobility of NPT(II) activity in bacterial extracts and cellular fractions following in situ localisation on a 10% non-denaturing polyacrylamide gel[47]. Lane 1, *E coli* extracts containing NPT(II), mixed with crude extract of green pGV3851-transformed tobacco tissue; lane 2, *E. coli* extract containing TP-NPT(II), mixed with crude extract of green, pGV3851-transformed tobacco tissue; lane 3, crude extract from green pGV3851-transformed tobacco tissue; lane 4, intact chloroplasts from green pGV3851-transformed tobacco tissue; lane 5, crude extract from green pGV3851::pLGV23neo-transformed tobacco tissue; lane 6, intact chloroplasts from green pGV3851::pLGV23neo-transformed tobacco tissue; lane 7, crude extract from green pGV3851::pGSSTneo3-transformed tobacco tissue; lane 8, intact chloroplasts from green pGV3851::pGSSTneo3-transformed tobacco tissue. P.K. (?): non-specific band present in untransformed plant tissue, probably due to the activity of plant kinase.

Methods: Three grams of green callus were homogenised by a few short bursts at low speed in a Waring Blendor in GR buffer (0.33 M sorbitol, 50 mM Hepes-KOH (pH 7.5), 1 mM $MgCl_2$; 1 mM MnCl2; 1 mM $MnCl_2$; 1 mM $Na_2$-EDTA, 2 mM $Na_2$-EDTA, 1 mg/ml isoacorbate, 0.5 mg/ml BSA). The homogenate was filtered through two layers of Miracloth and the filtrate was centrifuged from 0 to 4340×g and braked in the shortest possible time. The crude chloroplasts pellet was resuspended in a few ml of GR buffer. Intact chloroplasts were prepared from crude chloroplasts pellets by sedimentation in Percoll density gradients[53]. Gradient-purified intact chloroplasts were washed with GR and lysed in 25 mM Tris-HCl (pH 7.5) containing 0.5% β-mercapto ethanol.

Crude callus extracts were prepared by homogenizing 70 mg tissue in 70 μl extraction buffer (1% β-mercaptoethanol; 50 mM Tris; pH 6.8; 0.13 mg/ml leu-peptine) and clearing of the homogenate (2 minutes at 18,800 g). Crude extracts of *E. coli* were prepared by sonication in a buffer containing 10 mM Tris.HCl (pH 7.5); 10 mM $MgCl_2$; 25 mM $NH_4Cl$ and 10 mM $DTT^{ref.60}$, followed by centrifugation to remove cellular debris. The assay for NPT(II) activity is a modification of the in situ detection method described[47]. Samples diluted with a 10× loading buffer (50% glycerol; 0.5% SDS; 10% β-mercaptoethanol; 0.005% bromophenol blue) were separated on a 10% (w/v) nondenaturing polyacrylamide gel. After electrophoresis, the gel was washed twice for 10 minutes with distilled water and equilibrated for 30 minutes in 2× reaction buffer (100 mM Tris, pH 7.5; 50 mM $MgCl_2$; 400 mM $NH_4Cl$; 1 mM DTT). The gel was then transferred onto a glass plate and overlaid with a 1% agarose gel containing 30 μg/ml kanamycin sulphate and 200 μCi $\gamma^{32}$P-ATP in 1× reaction buffer. After 30 minutes at room temperature, the gel sandwich was covered with Whatman P81 phosphocellulose paper, two sheets of Whatman 3MM paper, and a stack of blotting paper pressed by weight (1 kg) to allow binding of the phosphorylated kanamycin to the P81 paper in a Southern-type transfer. After 3 hours the P81 paper was washed for 5 minutes with 500 ml hot water (80° C.), and for 3 hours several times with a 50 mM sodium phosphate buffer (pH 7.0). The p81 paper was dried and autoradiographed overnight using an intensifying screen to visualise the radio-labelled kanamycin formed at the position where the proteins with NPT(II) activity migrate in the polyacrylamide gel.

Figure 11:
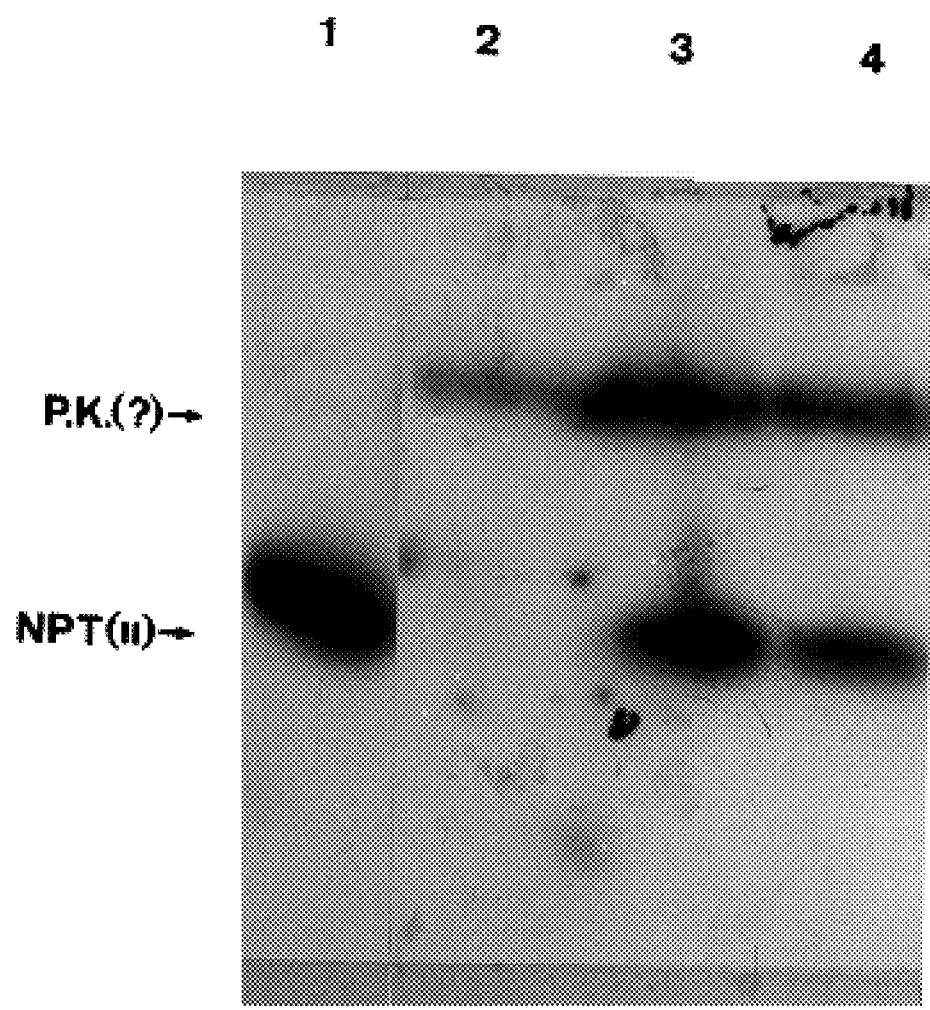
FIG. 11 is an autoradiogram showing the protection of the NPT(II) activity present within chloroplasts of pGV3851:pGSSTneo3-transformed tobacco cells to protease treatment as described in Example II.

6) Localization of NPT(II) activity in the stromal fraction of chloroplasts isolated from pGV3851::pGSSTneo3-transformed tobacco tissue (FIG. 11)

Intact chloroplasts were isolated from pGV3851::pGSSTneo3-transformed callus tissue and fractionated into stromal and membrane fractions. The NPT(II) activity associated with each of these fractions was assayed. Lane 1, *E. coli* extract containing NPT(II); lane 2, *E. coli* extract containing TP-NPT(II); lane 3, stromal fraction of chloroplasts isolated from green pGV3851::pGGSSTneo3-transformed tobacco tissue; lane 4, membrane fraction of chloroplasts in lane 3; lane 5, was of the membrane fraction shown in lane 4. P. K. (?), see FIG. 10.

Intact chloroplasts were isolated from greened tobacco tissue as described in the legend to FIG. 10. Chloroplasts washed twice with sorbitol-Hepes buffer and recovered by centrifugation were fractionated intro stroma and membrane portions by resuspending plastids in 25 mM Tris-HCl (pH 7.5) containing 0.5% β-mercaptoethanol followed by centrifugation at 18,800× g. Membrane fractions were twice washed and pelleted to remove residual stromal contamination. Wash fractions were routinely tested for residual NPT (II) activity.

Figure 12:
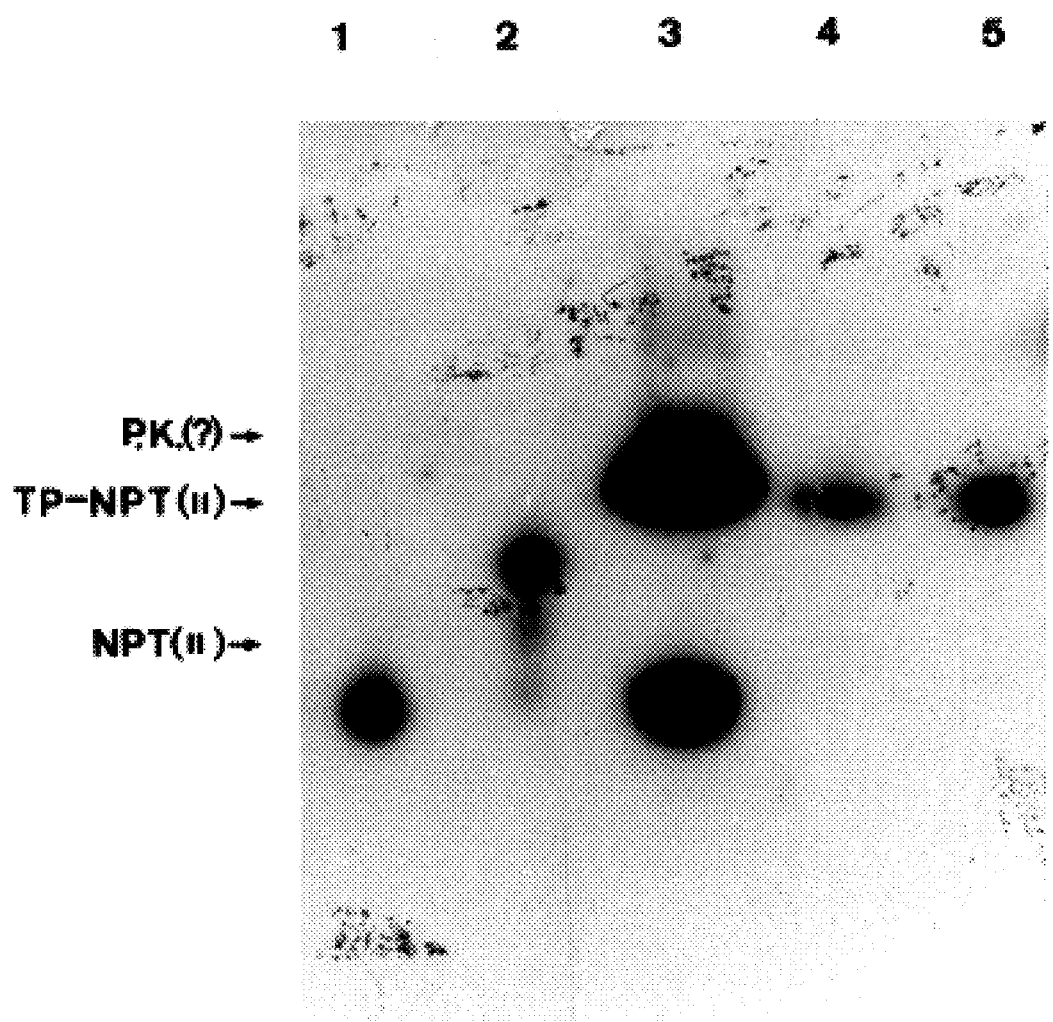
FIG. 12 is an autoradiogram showing the localization of NPT(II) activity in the stromal fraction of chloroplasts isolated from pGV3851:pGSSTneo3-transformed tobacco tissue as described in Example II.

7) Protection of the NPT(II) activity present within chloroplasts of pGV3851::pGSST-neo3-transformed tobacco cells to protease treatment (FIG. 12)

Intact chloroplasts isolated from pGV3851::pGSSTneo3-transformed tobacco callus tissue were subjected to limited proteolytic digestion and then fractionated into the stromal and membrane components. The protease insensitivity of NPT(II) activity associated with these fractions was assayed. Lane 1, *E. coli* extract containing NPT(II); lane 2, stromal fraction of intact chloroplasts isolated from green pGV3851::pGSSTneo3-transformed tobacco tissue and lysed before protease treatment; lane 3, stromal fraction on non-protease-treated intact chloroplasts isolated from green PGV3851::pGSSTneo3-transformed tobacco tissue; lane 4, stromal fraction of protease-treated intact chloroplasts isolated from green pGV3851:: pGSSTneo3-transformed tobacco tissue; P. K. (?), see FIG. 3.

Intact chloroplasts were prepared from greened tobacco callus tissue as described in the legend to FIG. 10. Protease treatment of isolated chloroplast was carried out as previously described[53]. Protease-treated and untreated plastids were fractionated as described in the legend to FIG. 5.

Figure 13:
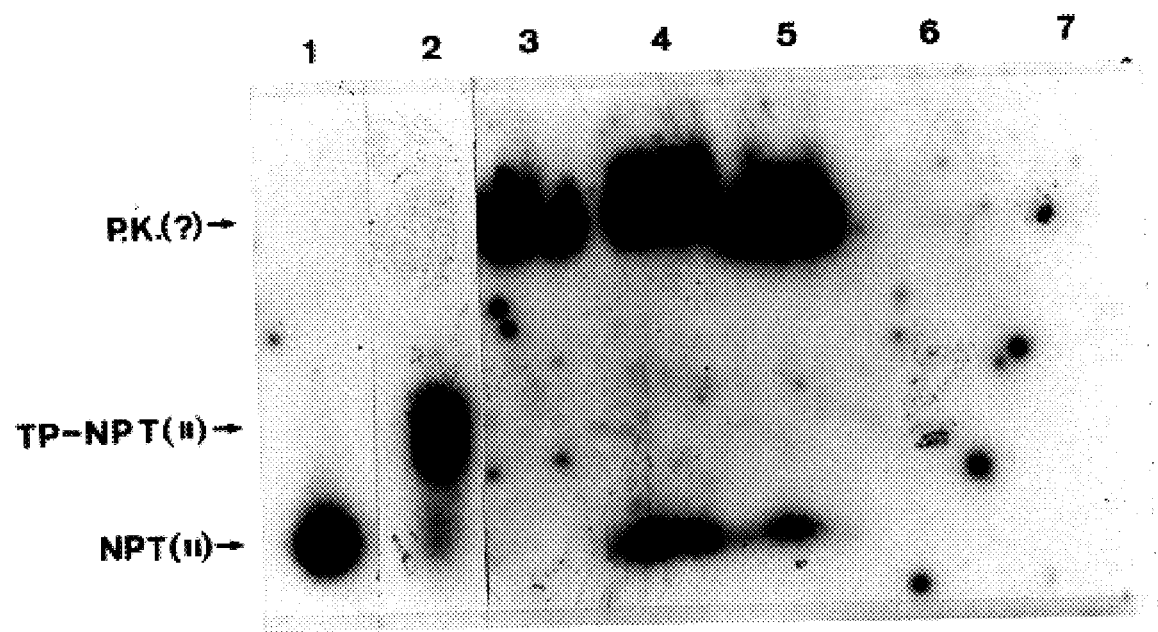
FIG. 13 is an autoradiogram showing the in vitro uptake of TP-NPT(II) fusion protein by isolated pea chloroplasts as described in Example II.

8) In vitro uptake of TP-NPT(II) fusion protein by isolated pea chloroplasts (FIG. 13)

An autoradiogram showing the in situ localization of NPT(II) activity in bacterial and chloroplast fractions following fractionation on non-denaturing polyacrylamide gels is presented. Lane 1, extract from *E. coli* harbouring pBR322::Tn5 (NPT(II)); lane 2, extract from *E. coli* harbouring pGLTneo1 (TP-NPT(II)); lane 3, stromal fraction of pea chloroplasts prior to incubation with bacterial extracts; lane 4, stromal fraction of pea chloroplasts incubated with bacterial extracts containing the TP-NPT(II) fusion protein; lane 5, stromal fractions of protease-treated pea chloroplasts (same amount as in lane 4) incubated with bacterial extracts containing the TP-NPT(II) fusion protein; lane 6, washed membrane fractions of the same chloroplasts as in lane 5; lane 7, washed membrane fraction of the same chloroplasts as in lane 4.

Methods

Intact chloroplasts were isolated from pea (*Pisum sativum*) leaves by sedimentation through Percoll density gradients[53]. Intact chloroplasts were washed and resuspended in sorbitol-Hepes buffer (50 mM Hepes-KOH, pH 7.5; 0.33 M sorbitol) and stored at 0° C. In vitro uptake into isolated chloroplasts was carried out essentially as described[53] except that the incubation mix was modified for use with bacterial extracts. Uptake reactions (300 µl final volume) contained intact chloroplasts (equivalent to 200–300 µg chlorophyll) and 50 µl of bacterial extract (as described in the legend to FIG. 10) in buffer containing 0.33 M sorbitol, 50 mM Hepes.KOH (pH 7.5), 1 mM $MgCl_2$, 1 mM $Na_2$-EDTA. Following incubation at 20–22° C. in the light with gentle shaking for 1 hour, chloroplasts were diluted with sorbitol-Hepes buffer and intact chloroplasts recovered by centrifugation at 4340× g. Chloroplasts washed twice with sorbitol-Hepes buffer and recovered by centrifugation were either fractioned immediately (see legend to FIG. 11) or subjected to protease treatment as previously described[53]. Aliquots of samples were either assayed immediately for NPT(II), or stored at −80° C. and assayed at a later time.

The results presented in this example from both the in vivo and in vitro studies clearly demonstrate that the NPT (II) component of the TP-NPT(II) fusion protein is translocated across the chloroplast envelope and is finally located in the stroma. The requirement of the transit peptide for this process is shown by the failure to detect uptake of NPT(II) by chloroplasts, when the transit peptide has not been fused to NPT(II). The TP-NPT(II) fusion protein, however, bears no similarity in the aminoacid sequence to the small subunit precursor, particularly near to the processing site thereof immediately following the transit peptide. This suggests that all of the sequence information required for translocation resides within the transit peptide.

Under normal physiological growth conditions for plants, the small subunit precursor is rapidly taken up and processed by the chloroplasts, and a large free pool of unprocessed precursor is not observed[1, 10]. It has been shown here, that in tobacco cells transformed with pGV3851::pGSSTneo3, all of the NPT(II) activity observed in either crude cellular extracts or isolated chloroplast fractions migrates on the gel system[47] used with similar electrophoretic mobility to the original NPT(II). Processing of the TP-NPT(II) fusion protein is presumably carried out by the same soluble, chloroplast-associated protease[18] that is responsible for the processing of the small subunit precursor. It seems likely, therefore, that the processing of the TP-NPT(II) fusion protein occurs at the same Cys/Met site (FIG. 8B) used in the small subunit precursor. Thus it can be hypothesized that the transit peptide can mediate not only translocation, but also site-specific processing. Furthermore, both the translocation and processing steps apparently occur rather efficiently in pGV3851::pGSSTneo3-transformed tobacco cells, since within the detection limits of our assay system, all of the NPT(II) activity observed corresponds to the processed form of the TP-NPT(II) fusion protein.

The results presented here again clearly demonstrate the applicability of using Agrobacterium-mediated cell transformation to introduce foreign genes into plants.

EXAMPLE III

Figure 14:
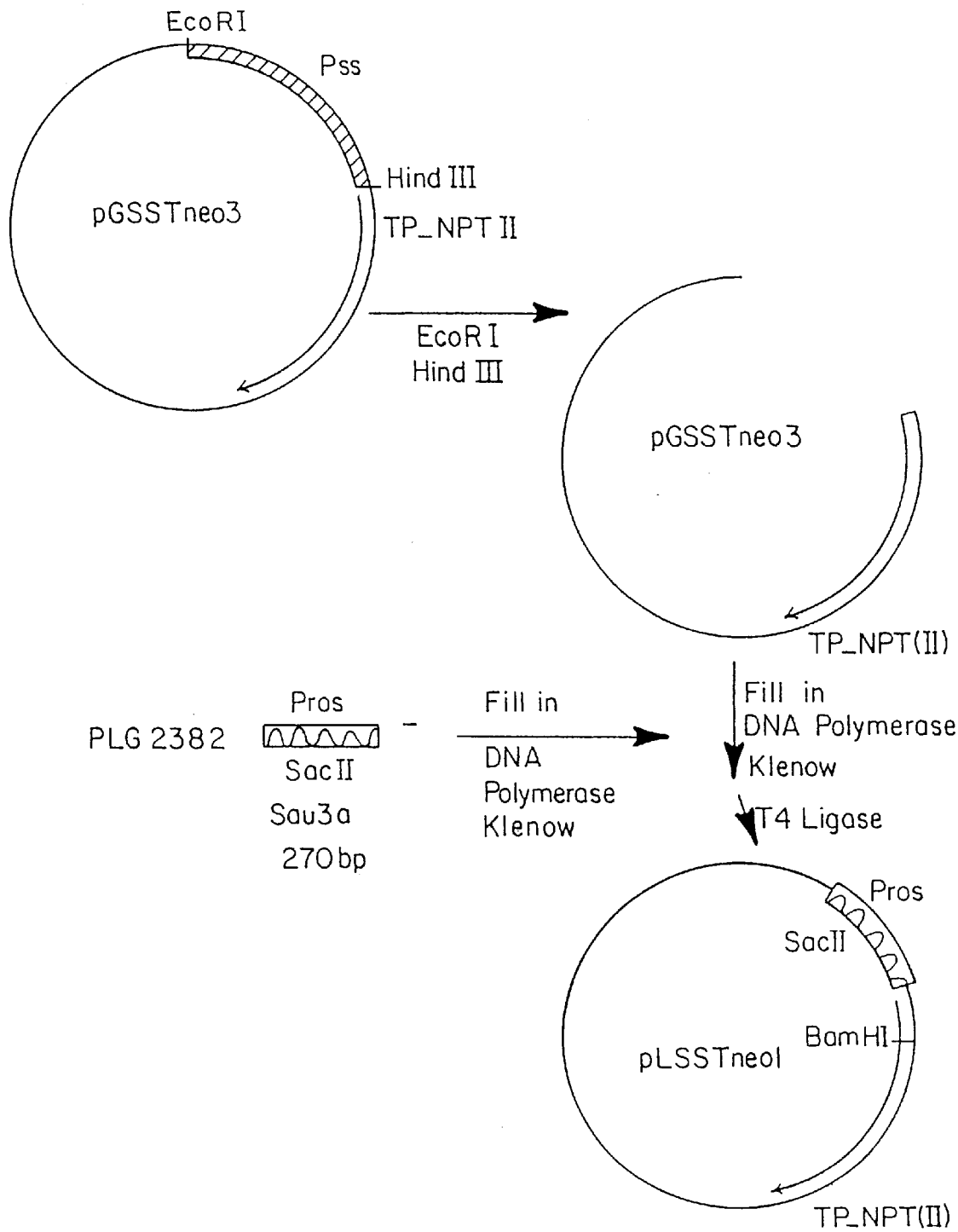
FIG. 14 shows the construction of a plasmid containing a chimeric gene encoding the TP-NPT(II) fusion protein and wherein the coding sequences are under control of a foreign promoter.

Construction of a plasmid encoding a chimaeric gene encoding the TP-NPT(II) fusion protein and wherein the coding sequences are under the control of a foreign promotor (FIG. 14)

The construction starts from pGSST neo3. This plasmid was then digested with EcoRI and Hind III. The staggered ends of the long fragments were filled in with the Klenow polymerase. The DNA obtained was then ligated to a SauIIIA fragment (270 bp) originating from plasmid pLGV 2382.

This SauIIIA fragment contains the promoter of the nopaline synthase (HERRERA-ESTRELLA L. et al (1983) Embo. J., 2, 987–995). The latter fragment was also treated with the klenow fragment of the DNA polymerase. The SauIIIA fragment so repaired and the repaired fragment from pGSSTneo3 were then ligated with T4 ligase, whereby plasmid pLSSTneo1 was obtained. The plasmid containing the promoter region oriented in the proper direction was identified by restriction analysis with the SacII restriction enzyme and BamHI. The plasmid (pLSSTneo1) which proved to contain the biggest SacII-BamHI fragment was also the one which contained the promoter region and the TP-NPT II fragment in the proper orientation and under control of said promoter.

There is thus, shown another plasmid having this time a constitutive promoter instead of the normal leaf specific light-inducible promoter. Consequently, a plasmid was obtained which can cause the protein located downstream of the promoter to be expressed also in the dark and also in other tissues of the plant. In such a manner one controls the level of production of metabolites of interest, for instance fatty acids or amino acids.

It will be appreciated that the invention also makes it possible to put a gene normally expressed under photosynthetic conditions under the control of a promoter which is normally operative in a constant manner (day and night). In such a way and for instance one can obtain the constant production of a determined amino acid under the control of a promoter operative in seeds.

The invention thus opens the way to important agricultural applications involving chloroplast functions. More particularly it enables the introduction of proteins of controlled structure in plant-cells chloroplast. These proteins can be introduced into the chloroplast either as such or as fusions with proteins or protein subunits which are coded for by natural genes and normally transported into the plant cell chloroplast. These proteins may either be proteins foreign to the plant cells to be transformed or be similar to endogenous proteins, yet different there from by controlled mutations. Particularly the invention now provides for the possibility of modifying at will genes including a determined protein, for instance for the sake of improving the activity of the enzyme encoded by the chloroplast genes. The invention also provides for the possibility of substituting another promoter for the endogenous promoter included in the natural gene to thereby regulate in a controlled manner the production of the chloroplast proteins.

The invention further provides valuable tools for a better understanding of the role played by various domains of transported proteins interacting with chloroplast coded proteins. It also renders possible the study of whether determined chimaeric genes can direct the transfer of proteins normally encoded by the chloroplast back into this organelle. Model systems of chloroplast-encoded genes of importance for basic research and agricultural application are readily available, such as the large subunit of RuBP carboxylase, which contains the catalytic site of the holoenzyme, or the 32 K protein conferring resistance to certain herbicides. The similarity between the results obtained from in vivo and in vitro studies also suggests that the production in *E. coli* of fusion proteins composed of segments of nuclear-encoded organelle polypeptides and an enzymatic reporter is a powerful technique for the rapid analysis of the signals and processes involved in protein import by isolated organelles.

The invention further provides the means which enables chimaeric engineering of plants with a potential for amino acid overproduction or improvement of plant productivity, and therefore meets needs which have already been recalled in the preamble of this application.

The use of transit peptides for specifically targeting polypeptides in the chloroplast also provides the possibility of genetically engineering genes containing sequences encoding key enzymes of given pathways in such manner that said key enzymes are no longer subjected to the normal regulation systems included in the natural plant cells.

The invention also provides means for solving other problems that have been mentioned in the preamble i.e. the production of herbicide resistant plants. Actually the invention now provides a method for fusion of a "second sequence" encoding the protein of interest with a first sequence encoding a transit peptide, the chimaeric gene so produced being capable after its insertion in the genetic DNA of the cells of the plant of interest to control the translocation of the protein of interest into the chloroplasts.

The invention opens the way to many other applications. A few additional examples are illustrated hereafter and in which the enzyme Ribulose bisphosphate carboxylase (RuBPCase) can be brought into play.

a) Improvement of the carboxylase/oxidase ratio

This enzyme catalyzes two enzymatic reactions:

1) The condensation of a molecule of Ribulose bisphosphate with a molecule of $CO_2$ to form two molecules of phosphoglyceric acid (Carboxylase reaction).

2) Reaction of a ribulose bisphosphate molecule with a molecule of oxygen to produce phosphoglycolate (oxidase reaction).

The latter is a competitive reaction with the carboxylation. Therefore it limits the efficiency of conversion of $CO_2$ into organic compounds.

The invention now provides a technique of site directed mutagenesis which allows the controlled alteration of a determined protein to be given full effect. For instance the modification of the RuBPCase in such a way that the carboxylase/oxidase ratio is much more favourable can now be contemplated. Another approach is to simply take a gene encoding for the RuBPCase from another plant or from another organism such as cyanobacteria which have a more favourable ratio, to fuse it with a nucleic acid fragment containing a promoter and a transit peptide effective in the plant of interest and to introduce the chimaeric gene obtained into said plant.

b) Improvement of plant productivity

There are several factors limiting plant productivity such as lack of nutrients and a low efficiency in light harvesting or $CO_2$ assimilation. Since the lack of nutrients can be solved using fertilizers, one of the main limiting factor for plant productivity becomes $CO_2$ assimilation. $CO_2$ uptake by a leaf depends mostly on two factors:

1) The physical diffusion of $CO_2$ along the plant cells and 2) the efficiency of $CO_2$ conversion to organic compounds.

Although different pathways for $CO_2$ assimilation exist in higher plants, they share the same limiting step, which is the efficiency of the RuBPCase enzyme. Here again the invention provides means for overcoming this problem at least in part, for instance upon introducing in the cells of the plant a chimaeric gene comprising sequences fused with one another and which respectively contain a promoter region and a fragment encoding a transit peptide which are particularly effective in that plant, on the one hand, and a sequence encoding a more efficient RuBPCase and originating from another plant, on the other hand.

Cultures comprising plasmids, intermediate cloning vectors, and microorganisms prepared by the processes of this invention are exemplified by cultures deposited in the German Collection of Microorganisms (DSM), Güttingen, Germany. These cultures are identified hereafter:

(1) *E. coli* HB101 (pSRP6)

(2) *E. coli* HB101 (pKM 109/9)

(3) *E. coli* HB101 (pGSST3)

These cultures were deposited on Dec. 27, 1984.

These cultures were assigned accession numbers 3172 (1) 3171 (2) 3170 (3).

Other cultures referred to in this application have also been deposited on or before December 27th, i.e. on Dec. 20th, 1984. Plasmids were maintained in the microorganisms identified in the left hand part of the table hereafter.

These cultures have been assigned the following accessing numbers:

| Internal Code/ Taxonomic Designation | Plasmid in strain | DSM No. |
|---|---|---|
| AZ 1/ *E. coli* K12 and VII | p PSR 6 delta R V | 3161 |
| AZ 2/ *E. coli* K12 and VII | p I-22 | 3162 |
| AZ 3/ *E. coli* and VII | p II-4 | 3163 |
| AZ 4/ *E. coli* K12 and VII | pGV 710 | 3164 |

-continued

| Internal Code/<br>Taxonomic Designation | Plasmid<br>in strain | DSM No. |
|---|---|---|
| AZ 5/<br>AGR. TUMEF. VII | pGV 3850::pSNIPP | 3165 |
| AZ 6/<br>AGR. TUMEF. | pGV 3850::pSNIF | 3166 |
| AZ 7/<br>AGR. TUMEF. VII | pGV 3850 | 3167 |

REFERENCES

Apel, K. and Kloppstech, K. (1978) Eur. J. Biochem, 44, 491–503.

Aviv, H., and Leder, P. (1972) Proc. Natl. Acad. Sci. USA 69, 1408–1412.

Bailey, J. M. and Davidson, N. (1976) Analyt. Biochem. 70, 75–85.

Bartlett, S. G., Grossman, A. R., and Chua, N.-H (1982), In: (Edelman, M. Hallick, R. B., and Chua, N.-H, eds) Methods in Chloroplast Molecular Biology, Elsevier Biomed. Press, Amsterdam-New York-Oxford, 1081–1091.

Beck, E., Ludwig, E. A., Auerswald, B., Reiss, B. and Schaller, H. (1982) Gene 19, 327–336.

Bedbrook, J. (1981) Plant Molec. Biol. Newsletter 2, 24.

Berry-Lowe, S. L., McKnight, T. D., Shah, D. M., and Meagher, R. B. (1982) J. Mol. Appl. Genet. 1, 483–498.

Bevan, M. W., Flavell, R. B., Chilton, D. (1983) Nature 304, 184–187.

Bohnert, J. J., Crouse, E. J. Pouyet, J., Mucke, H., and Loeffelhardt, W. (1982) Eur. J. Biochem. 126, 381–388.

Broglie, R. Coruzzi, G., Fraley, R. T., Rogers, S. G., Horsch, R. B., Niedermeyer, J. C., Fink, C. L., Flick, J. S. and Chua, N.-H. (1984) Science 224, 838–843.

Broglie, R., Coruzzi, G., Lamppa, G., Keith, B., and Chua, -H. (1983) Bio/Technology 1, 55–61.

Capaldi, R. A. and Vanderkooi, G. (1972) Proc. Natl. Acad. Sci. 69, 930–932.

Caplan, A., Herrera-Estrella, L., Inze, D., Van Haute, E., Van Montagu, M., Schell, J., and Zambryski, P. (1983) Science (Wash.) 222, 815–821.

Cashmore, A. R. (1983) In: (Kosuge, T., Meredith, C. P., Hollaender, A., eds), Genetic Engineering of Plants—An Agricultural Perspective, Plenum, New York, 29–38.

Cashmore, A. R. (1984) Proc. Natl. Acad. Sci. USA 81, 2960–2964.

Chirgwin, J. M., Przybla, A. E., McDonald, R. J., Rutter, W. J. (1979) Biochemistry 24, 5294–5299.

Chua, N.-H., and Schmidt, G. W. (1978) Proc. Natl. Acad. Sci. USA 71, 6110–6114.

Chua, N.-H., Grossman, A. R., Bartlett, S. G., and Schmidt, G. W. (1980) Sythesis, transport and assembly of chloroplast protein. In: "Biological chemistry of organelle formation", Th Bucher, W. Sebald, and H. Weiss (Eds.) Berlin, Springer-Verlag, 113–117.

De Block M., Herrera-Estrella L., Van Montagu M., Schell J., and Zambrisky P. (1984) EMBO J 3, 1681–1690.

De Greve, H., Dhease, P., Seurinck, J., Lemmers, M., Van Montagu, M., and Schell, J. (1983). Molec. Appl. Genet. 1, 499–511.

Dhaese, P., De Greve, H., Gielen, J., Seurinck, J., Van Montagu, M., and Schell, J. (1983) EMBO J. 2, 419–426.

Dron, M., Rahire, M., Rochaix, J.-D., and Mets, L. (1983) Plasmid 9, 321–324.

Ellis, R. J. (1981) Ann. Rev. Physiol. 32, 11–137.

Ellis, R. J., and Robinson, C. (1984) In: (Freedman, R. B., and Hawkins, H. C., eds) The Enzymology of the Post-translational Modification of Proteins, Academic Press, New York, in press.

Fraley, R. T., Rogers, S. G., Horsch, R. B., Sanders, P. R., Flick, J. S., Adams, S. P., Bittner, M. L., Brand, L. A., Fink, C. L., Fry, J. S., Gallupi, G. R., Goldberg, S. B., Hoffman, N. L., and Woo, S. C. (1983) Proc. Natl. Acad. Sci. USA 80, 4803–4807.

Gray, C. J. (1982), In: (Edelman, M. Hallick, R. B., and Chua, N.-H., eds) Methods in Chloroplast Molecular Biology, Elsevier Biomed. Press, Amsterdam-New York-Oxford, 1081–1091.

Hamer. D. H., and Leder P. (1978), Cell 18, 1299–1302.

Herrera-Estrella, L., Depicker, A., Van Montagu, M., and Schell, J. (1983), Nature 303, 209213.

Herrera-Estrella, L., Van den Broeck, G., Maenhaut, R., Van Montagu, M., Schell, J., Timko, M., and Cashmore, A. (1984), Nature 310, 115–120.

Hain, R., Stabel, P., Czernilofsky, A. P., Steinbiss, H. H., and Schell, J. submitted for publication to Mol. Gen. Genet.

Joos, H., Inze, D. Caplan, A. Sormann, M. Van Montagu, M. and Schell, J. (1983) Cell 32, 1057–1067.

Laemmli, U. K. (1970) Nature 227, 680–685.

Maniatis, T., Fritsch, E. F., Sambrook, J. (1982) Molecular Cloning, Cold Spring Harbor Laboratory Press, Cold Spring Harbor.

Marton, L. Wullems, G. J., and Schilperoort, R. A. (1979) Nature 277, 129–131.

Maxam, A. M., and Gilbert, W. (1977) Proc. Natl. Acad. Sci. USA 74, 560–564.

Murashige, T., and Skoog, F. (1962) Physiol. Plant 15, 473–479.

Otten, L. (1982) Plant Sci Lett. 25, 15–27.

Ortiz, W., Reardon, E. M., and Price, C. A. (1980) Plant Physiol. 66, 291–294.

Reiss, B., Sprengel, R., Will, H., and Schaller, H. (1984a) Gene 30, 211–218.

Reiss, B., Spengel, R. and Schaller, H. (1984b) EMBO J. 13.

Robinson, C., and Ellis, R. J. (1984) Europ. J. Biochem. 142, 343–346.

Schmidt, G. W., Devillers-Thiery, A., Desruisseaux, H, Blobel, G. and Chua, N.-H. (1979) J. Cell Biol. 83, 615–622.

Schmidt, G. W., Bartlett, S. G., Grossman, A. R., Cashmore, A. R. & Chua, N.-H. (1981) J. Cell Biol. 91, 468–478.

Somerville, S. C., and Ogren, W. L. (1983) Proc. Natl. Acad. Sci. USA 80, 1290–1294.

Southern, E. M. J. Mol. Biol. (1975) 98, 503–518.

Spreitzer, R. J., and Ogren, W. L. (1983) Proc. Natl. Acad. Sci. USA 80, 6293–6297.

Stiekema, W. J., Wimpee, Ch. F., and Tobin, M. (1983) Cell 11, 8051–8061.

Thomas, P. S. (1983) Methods Enzymol. 100, 255–266.

Timko, M. P. and Cashmore, A. R. (Alan R. Liss, New York, 1983) in Plant Molec. Biol. (ed. Goldberg, R. B. ) 403–412.

Van den Broeck, G., Timko, M. P., Kausch, A. P., Cashmore, A. R., Van Montagu, M. and Herrera-Estrella, L. Nature (in press).

Van Haute, E. Joos, H., Maes, M., Warren, H. G., Van Montagu, M., and Schell, J. (1983) EMBO J. 2, 411–418.

Willmitzer, L., Dhaese, P., Schreier, P. H., Schmalebach, W., Van Montagu, M., and Schell, J. (1983) Cell 32, 1045–1056.

Zambryski, P., Herrera-Estrella, L., Block, M., Van Montagu, M., and Schell, J. (1984) In: (Hollaender, A., and Setlow, J., eds) Genetic Engineering, Principles and Methods, vol. 6, Plenum, New York, in press.

Zambryski, P., Joos, H., Genetello, C., Leemans, J., Van Montagu, M., and Schell, J. (1983) EMBO J. 2, 2143–2150.

Zurawski, G., Perrot, B., Bottomley, W., and Whitfeld, P. R. (1981) Nucleic Acids Res. 9, 3251–3270.

REFERENCES

1. Ellis, R. J. *Annu. Rev. Plant Physiol.* 32, 111–137 (1981).
2. Gillham, N., Boynton, J. & Chua, N. -H. *Curr. Top. Bioeng.* 8, 211–260 (1978).
3. Gray, J. C. & Kekwick, R. G. O. *Eur. J. Biochem.* 44, 491–503 (1974).
4. Cashmore, A. *J. Biol. Chem.* 251, 2848–2853 (1976).
5. Apel, K. & Kloppstech, K. *Eur. J. Biochem.* 85, 581–588 (1978).
6. Highfield, P. E. & Ellis, R. J. *Nature* (London) 271, 420–424 (1978).
7. Dobberstein, B., Blobel, G. & Chua, N. -H. *Proc. Acad. Sci. USA* 74, 1082–1085 (1977).
8. Schmidt, G. W., Bartlett, S. G., Grossman, A. R., Cashmore, A. R. & Chua, N. -H. *J. Cell Biol.* 91, 468–478 (1981).
9. Cashmore, A. R., Broadhurst, M. K. & Gray, R. E. *Proc. Natl. Acad. Sci. USA* 75, 655–659 (1978).
10. Chua, N. -H. & Schmidt *J. Cell Biol.* 81, 461–483 (1979).
11. Chua, N. -H. & Schmidt, G. W. *Proc. Natl. Acad. Sci. USA* 75, 6110–6114 (1978).
12. Ellis, R. J., Smith, S. M. & Barraclough, R. in *Genome Organization and Expression in Plants* (eds Leaver, C. J.) 321–335 (Plenum Press, New York, 1980).
13. Schmidt, G. W., Bartlett, S. G., Grossman, A. R., Cashmore, A. R. & Chua, N. -H. in *Genome Organization and Expression in Plants* (eds Leaver, C. J.) 337–351 (Plenum Press, New York, 1980).
14. Grossman, A. R., Bartlett, S. G., Schmidt, G. W., Mullet, J. E. & Chua, N. -H. *J. Biol. Chem.* 257, 1558–1563 (1982).
15. Grossman, A. R., Bartlett, S. G., Schmidt, G. W. & Chua, N. -H. *Ann. N.Y. Acad Sci* 342, 266–274 (1980).
16. Chua, N. -H & Schmidt, G. W. in *Photosynthetic Carbon assimilation* (eds Siegelman, H. W. and Hind, G.) 325–347 (Plenum Press, New York, 1978).
17. Grossman, A. R., Bartlett, S. G. & Chua, H. -H. *Nature* (London) 285, 625–628 (1980).
18. Robinson, C. & Ellis, J. R. *Eur. J. Biochem.* 142, 343–346 (1984).
19. Schmidt, G. W. et al. *J. Cell Biol.* 83, 615–622 (1979).
20. Broglie, R., Coruzzi, G., Lamppa, G., Keith, B. & Chua, N. -H. *Bio/technology* 1, 55–61 (1983).
21. Timko, M. P. & Cashmore, A. R. in *Plant Molecular Biology* (ed. Goldberg, R. B.) 403–412 (Alan R. Liss, New York, 1983).
22. Coruzzi, G., Broglie, R., Lamppa, G. & Chua, N. -H. in *Structure and function of plant genomes* (eds Ciferri, O. and Dure III, L.) 47–59 (Plenum Press, New York, 1984).
23. Broglie, R. et al. *Science* 224, 838–843 (1984).
24. Bartlett, S. B., Grossman, A. R. & Chua, N. -H. in *Photosynthesis* (ed. Akoyonoglou, G.). 43–.. (Baladan, New York, 1980).
25. Silhavy, T. J. et al. *Proc. Natl. Acad. Sci. USA* 74, 5411–5415 (1977).
26. Wolfe, P. B. & Wickner, W. *Cell* 36, 1067–1072 (1984).
27. Gething, M. -J. & Sambrook, J. *Nature* (London) 300, 598–603 (1982).
28. Sabatini, D. D., Kreibich, G., Morimoto, T. & Adesnik, M. *J. Cell Biol* 92, 1–22 (1982).
29. Emr, S. D. & Silvahy, T. *J. Cell Biol.* 95, 689–696 (1982).
30. Benson, S. A. & Silvahy, T. *Cell* 32, 1325–1335 (1983).
31. Guarente, L. & Ptashne, M. *Proc. Natl. Acad. Sci. USA* 78, 2460–2464 (1981).
32. Hall, M. N., Hereford, L. & Herskowitz, I. *Cell* 36, 1057–1065 (1984).
33. Lignappa, V. R., Chaidez, J., Yost, C. S. & Hedpeth, J. *Proc. Natl. Acad. Sci. USA* 81, 456–460 (1984).
34. Douglas, M. G., Geller, B. L. & Emr, S. S. *Proc. Natl. Acad. Sci. US* 81, 3983–3987 (1984).
35. Herrera-Estrella, L., Depicker, A., Van Montagu, M. & Schell, J. *Nature* (London) 303, 209–213 (1983).
36. Fraley, R. T. et al. *Proc. Natl. Acad. Sci. USA* 80, 4803–4807 (1983).
37. Horsch, R. B. et al. *Science* 223, 496–498 (1984).
38. Bevan, M. W., Flavell, R. B. & Chilton, M. -D. *Nature* (London) 304, 184–187 (1983).
39. Murai, N. et al. *Science* 222, 476–482 (1983).
40. Herrera-Estrelia, L. et al. *EMBO J.* 2, 987–995 (1983).
41. Caplan, A. et al. *Science* 222, 815–821 (1983).
42. Herrera-Estrella, L. et al. *Nature* (London) 310, 115–120 (1984).
43. De Block, M. et al. *EMBO J.* 3, 1681–1689 (1984)
44. Cashmore, A. R. in *Genetic Engineering of Plants—an agricultural perspective* (eds Kosuge, T., Meredith, C. P. & Hollaender, A.) 29–38 (Plenum Press, New York, 1983).
45. Reiss, B. Ph.D. Thesis, Heidelberg (1982).
46. Beck, E., Ludwig, G., Auerswald, E. A., Reiss, B. & Schaller, H. *Gene* 19, 327–336 (1982).
47. Reiss, B., Sprengel, R., Will, H. & Schaller H. *Gene* 30, 217–223 (1984).
48. Zambryski, P., Herrera-Estrella, L., De Block, M., Van Montagu, M. & Schell, J. in *"Genetic engineering, Principles and Methods"* (Vol. 6) (eds Setlow, J. & Hollaender, A.) 253–278 (Plenum Press, New York, 1984).
49. Van Haute, E. et al. *EMBO J.* 2, 411–418 (1983).
50. Southern E. M. *J. Mol. Biol.* 98, 503–518 (1975).
51. Schröder. G., Waffenschmidt, S., Weiler, E. W. & Schröder, J. *Eur. J. Biochim.* 138, 387–391 (1984).
52. Murashige, T. & Skoog, F. *Physiol. Plantarum* 15, 473–497 (1962 ).
53. Bartlett, S. G., Grossman, A. R. & Chua, N. -H. in *Methods in Chloroplast Molecular Biology* (ed M. Edelman) 1081–1091 (Amsterdam Elservier Biomedical Press, 1982).
54. Walter, P. & Blobel, G. *Proc. Natl. Acad. Sci. USA* 77, 7112–7116 (1980).
55. Lathe, R., Balland, A., Kohli, V. & Lecocq, J. -P. *Gene* 20, 187–195 (1982).
56. De Greve, H. et al. *J. Mol. Appl. Genet.* 1, 499–512 (1982).
57. Vieira, J. & Messing, J. *Gene* 19, 259–268 (1982).
58. Dhaese, P. et al. *EMBO J.* 2, 419–426 (1983).
59. Dellaporta, S. L., Wood, J. & Hicks, J. B. *Plant Mol. Biol Reporter* 1, 19–21 (1983).
60. Haas, M. J. & Dowding, J. E. *Meth. Enzymol.* 43, 611–628 (1975).

We claim:

1. A plant comprising in its nuclear genome a chimaeric DNA sequence, comprising:
   a.) a nucleic acid sequence coding for a chimaeric protein or polypeptide comprising:
      i.) a transit peptide of a cytoplasmic precursor of a chloroplast protein or chloroplast polypeptide of a plant species; and
      ii.) a protein or polypeptide of interest which is different from the polypeptide or protein normally associated with said transit peptide in a cytoplasmic precursor, wherein said transit peptide is located in the amino-terminal part of said chimaeric protein or polypeptide; and
   b.) a promoter upstream of said nucleic acid sequence recognized by polymerases endogenous to said plant; wherein the chimaeric DNA sequence can be expressed in cells of said plant under control of said promoter, and said protein or polypeptide of interest is translocated into chloroplasts of cells of said plant.

2. The plant of claim 1, in which said protein or polypeptide of interest confers resistance to an herbicide.

3. The plant of claim 2, in which said protein or polypeptide of interest is an acetolactate synthase.

4. The plant of claim 2, in which said protein or polypeptide of interest is 5-enol pyruvyl-3-phosphoshikimate synthase.

5. The plant of claim 1, in which said protein or polypeptide of interest is of bacterial origin.

6. The plant of claim 1, in which said protein or polypeptide of interest is of plant origin.

7. The plant of claim 1, in which the first amino acid of said protein or polypeptide of interest is a methionine.

8. The plant of claim 1, in which no more than the first seven amino acids of said protein or polypeptide of interest are encoded by a synthetic nucleotide linker.

9. The plant of claim 1, in which said transit peptide is from a cytoplasmic precursor of a chloroplast protein selected from the group consisting of the small subunit of ribulose-1,5-bisphosphate carboxylase, and chlorophyll a/b binding protein.

10. The plant of claim 9, in which the transit peptide is from a cytoplasmic precursor of the small subunit of ribulose-1,5-bisphosphate carboxylase of a plant selected from the group consisting of soybean, pea, duckweed, and wheat.

11. The plant of claim 9 in which the transit peptide has the sequence selected from the group consisting of the amino acid sequence of SEQ ID No 2 and the amino acid sequence of SEQ ID No 4.

12. The plant of claim 1, in which said promoter is normally associated with the DNA encoding said transit peptide.

13. The plant of claim 12, in which said promoter is a promoter of a gene selected from the group consisting of the plastocyanin gene, the ferredoxin- NADP+oxydoreductase gene, the ribulose-1,5-bisphosphate carboxylase gene, and the chlorophyll a/b binding protein gene.

14. The plant of claim 1, in which said promoter is foreign to the DNA encoding said transit peptide.

15. The plant of claim 14, in which said promoter is a promoter of the nopaline synthase gene.

16. A plant comprising in its nuclear genome a chimaeric DNA sequence comprising:
   a.) a nucleic acid sequence coding for a chimaeric protein or polypeptide comprising in sequence:
      (1) a transit peptide of a cytoplasmic precursor of a chloroplast protein or chloroplast polypeptide of a plant species, and
      (2) a hybrid protein comprising in sequence:
         (i) a linker, and
         (ii) a protein or polypeptide of interest which is different from the polypeptide or protein normally associated with said transit peptide in said cytoplasmic precursor wherein said linker does not significantly alter the biological property of said protein or polypeptide of interest in said hybrid protein, and b.) a promoter upstream of said nucleic acid sequence recognized by polymerases endogenous to a plant, wherein the chimaeric DNA sequence is expressed in cells of said plant under the control of said promoter, and said hybrid protein is translocated into the chloroplasts of said cells of the plant.

17. The plant of claim 16, wherein said linker is a N-terminal part of a chloroplast protein or chloroplast polypeptide derived from a natural cytoplasmic precursor thereof by proteotypical removal of its transit peptide.

18. The plant of claim 16, in which said protein or polypeptide of interest is of bacterial origin.

19. The plant of claim 16, in which said protein or polypeptide of interest is of plant origin.

20. The plant of claim 16, in which said protein or polypeptide of interest confers resistance to an herbicide.

21. The plant of claim 16, in which said protein or polypeptide of interest is an acetolactate synthase.

22. The plant of claim 16, in which said protein or polypeptide of interest is 5-enol pyruvyl-3-phosphoshikimate synthase.

23. The plant of claim 16, in which said N-terminal part is encoded by a DNA sequence that comprises an intron.

24. The plant of claim 16, in which said transit peptide is from a cytoplasmic precursor of a chloroplast protein selected from the group consisting of the small subunit of ribulose-1,5-bisphosphate carboxylase, and chlorophyll a/b binding protein.

25. The plant of claim 24, in which the transit peptide is from a cytoplasmic precursor of the small subunit of ribulose-1,5-bisphosphate carboxylase of a plant selected from the group consisting of soybean, pea, duckweed and wheat.

26. The plant of claim 24, in which the transit peptide has the sequence selected from the group consisting of the amino acid sequence of SEQ ID No 2 and the amino acid sequence of SEQ ID No. 4.

27. The plant of claim 16, in which said promoter is normally associated with the DNA encoding said transit peptide.

28. The plant of claim 27, in which said promoter is a promoter of a gene selected from the group consisting of the plastocyanin gene, the ferredoxin-NADP+oxydoreductase gene, the ribulose-1,5-bisphosphate carboxylase gene, and the chlorophyll a/b binding protein gene.

29. The plant of claim 16, in which said promoter is foreign to the DNA encoding said transit peptide.

30. The plant of claim 29, in which said promoter is a promoter of the nopaline synthase gene.

31. A plant comprising in its genome a chimaeric DNA sequence comprising:
  a.) a nucleic acid sequence coding for a chimaeric protein or polypeptide comprising in sequence:
    (1) a transit peptide of a cytoplasmic precursor of a chloroplast protein or chloroplast polypeptide of a plant species, and,
    (2) a fusion protein comprising in sequence,
      (i) a N-terminal part consisting of no more than the first 22 N-terminal amino acids of the amino acid sequence of a cytoplasmic precursor of a chloroplast protein or polypeptide after prototypical removal of its transit peptide upon translocation into the chloroplast of a cell of a plant,
      (ii) a protein or polypeptide of interest which is different from the polypeptide or protein normally associated with said transit peptide, and,
  b.) a promoter upstream of said nucleic acid sequence recognized by polymerases endogenous to said plant, wherein the chimaeric DNA sequence is expressed in cells of said plant under the control of said promoter, and said fusion protein is translocated into the chloroplasts of said cells of said plants.

32. An image forming aparatus on which at least one set of ink jet recording heads is mountable, each of the ink jet recording heads of a same set discharging one of a plurality of inks which belong to a same color family and have different densities, ink jet recording heads of a same set comprise a thick ink jet recording head associated with thick ink of one color family, and a thin ink jet recording head associated with thin ink of the one color family, the image forming apparatus comprising:

detecting means for detecting a failure of ink discharge of the ink jet recording heads;

mode selecting means for selecting, in response to a detection signal outputted from said detecting means, a recording mode of the ink jet recording heads from among i) a mode to use both of thick and thin ink, ii) a mode to use only thin ink, and iii) a mode to use only thick ink;

first control means for controlling the driving of the ink jet recording heads in accordance with a recording mode selected by said mode selecting means; and second control means for setting a recording density on a recording medium in accordance with the mode selected by the mode selection means, wherein said mode selecting means selects the mode which uses only thick ink from the thick ink head of each set if the detection signal indicates that ink discharge of the thin ink head has failed, and the mode which uses only thin ink from the thin ink head of each set if the detection signal indicates that ink discharge of the thick ink head has failed.

33. The plant of claim 31, in which said protein or polypeptide of interest is of plant origin.

34. The plant of claim 31, in which said protein or polypeptide of interest confers resistance to an herbicide.

35. The plant of claim 34, in which said protein or polypeptide of interest is an acetolactate synthase.

36. The plant of claim 34, in which said protein or polypeptide of interest is 5-enol pyruvyl-3-phosphoshikimate synthase.

37. The plant of claim 31, in which said N-terminal part is encoded by a DNA sequence that comprises an intron.

38. The plant of claim 31, in which said N-terminal part is from the small subunit of the ribulose-1,5-bisphosphate carboxylase of *Pisum sativum*.

39. The plant of claim 31, in which said N-terminal part consists of no more than the first five N-terminal amino acids of said amino acid sequence of a cytoplasmic precursor of a chloroplast protein or polypeptide after proteotypical removal of its transit peptide upon translocation into the choroplast of a cell of a plant.

40. The plant of claim 39, in which said N-terminal part has the sequence M-Q-V-W-P.

41. The plant of claim 31, in which said transit peptide is from a cytoplasmic precursor of a chloroplast protein selected from the group consisting of the small subunit of ribulose-1,5-bisphosphate carboxylase, and chlorophyll a/b binding protein.

42. The plant of claim 31, in which the transit peptide is from a cytoplasmic precursor of the small subunit of ribulose-1,5-bisphosphate carboxylase of a plant selected from the group consisting of soybean, pea, duckweed, and wheat.

43. The plant of claim 31 in which the transit peptide has the sequence selected for the group consisting of the amino acid sequence of SEQ ID No 2 and the amino acid sequence of SEQ ID No. 4.

44. The plant of claim 31, in which said promoter is normally associated with the DNA encoding said transit peptide.

45. The plant of claim 44, in which said promoter is a promoter of a gene selected from the group consisting of the plastocyanin gene, the ferredoxin-NADP+oxydoreductase gene, the ribulose-1,5-bisphosphate carboxylase gene, and the chlorphyll a/b binding protein gene.

46. The plant of claim 31, in which said promoter is foreign to the DNA encoding said transit peptide.

47. The plant of claim 46, in which said promoter is a promoter of the nopaline synthase gene.

48. A seed of the plant of any one of claims 1 to 6, 9, 16, 17, and 31, comprising said chimaeric DNA sequence.

49. A cell of the plant of any one of claims 1 to 6, 9, 16, 17, and 31, comprising said chimaeric DNA sequence.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 171 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: Pisum sativum (ix) FEATURE:
       (A) NAME/KEY: -
       (B) LOCATION:1..171
       (D) OTHER INFORMATION:/note= "transit peptide associated
          with the small subunit of RuBP of pea c..."

(xi) SEQUENCE DESCRIPTION: SEQ ID NO: 1:

```
ATGGCTTCTA TGATATCCTC TTCCGCTGTG ACAACAGTCA GCCGTGCYTC TAKGGGGCAA      60

TCCGCSGCAG TGGCTCCATT CGGCGGCCTS AAATCCATGA CTGGATTCCC AGTGAAGAAG     120

GTCAACACTG ACATTACTTC CATTACAAGC AATGGTGGAA GAGTAAAGTG C              171
```

(2) INFORMATION FOR SEQ ID NO: 2:

(i) SEQUENCE CHARACTERISTICS:
       (A) LENGTH: 57 amino acids
       (B) TYPE: amino acid
       (C) STRANDEDNESS:
       (D) TOPOLOGY: linear (ii) MOLECULE TYPE: peptide (vi) ORIGINAL SOURCE:
       (A) ORGANISM: Pisum sativum (ix) FEATURE:
       (A) NAME/KEY: Peptide
       (B) LOCATION:1..57
       (D) OTHER INFORMATION:/note= "transit peptide of the
          small subunit of RuBP of pea cells."

(xi) SEQUENCE DESCRIPTION: SEQ ID NO: 2:

```
Met Ala Ser Met Ile Ser Ser Ser Ala Val Thr Thr Val Ser Arg Ala
1               5                  10                  15

Ser Arg Gly Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys
    50                  55
```

(2) INFORMATION FOR SEQ ID NO: 3:

(i) SEQUENCE CHARACTERISTICS:
       (A) LENGTH: 108 base pairs
       (B) TYPE: nucleic acid
       (C) STRANDEDNESS: double
       (D) TOPOLOGY: linear (ii) MOLECULE TYPE: DNA (genomic)

```
    (ix) FEATURE:
          (A) NAME/KEY: -
          (B) LOCATION:1..108
          (D) OTHER INFORMATION:/note= "transit peptide  of the
              chlorophyll a/b-protein complex"

(xi) SEQUENCE DESCRIPTION: SEQ ID NO: 3:

ATGGCCGCAT CATCATCATC ATCCATGGCT CTCTCTTCTC CAACCTTGGC TGGCAAGCAA      60

CTCAAGCTGA ACCCATCAAG CCAAGAATTG GGAGCTGCAA GGTTCACC                  108

(2) INFORMATION FOR SEQ ID NO: 4:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Peptide
         (B) LOCATION:1..36
         (D) OTHER INFORMATION:/note= "transit peptide of the
             light harvesting chlorophyll a/b protein complex"

(xi) SEQUENCE DESCRIPTION: SEQ ID NO: 4:

Met Ala Ala Ser Ser Ser Ser Ser Met Ala Leu Ser Ser Pro Thr Leu
1               5                   10                  15

Ala Gly Lys Gln Leu Lys Leu Asn Pro Ser Ser Gln Glu Leu Gly Ala
            20                  25                  30

Ala Arg Phe Thr
        35

(2) INFORMATION FOR SEQ ID NO: 5:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (vi) ORIGINAL SOURCE:
         (A) ORGANISM: Pisum sativum (ix) FEATURE:
         (A) NAME/KEY: Peptide
         (B) LOCATION:1..18
         (D) OTHER INFORMATION:/note= "region around the
             processing site of the precursor to the small subunit
             polypeptide of Rubisco encoded by the pea ss3.6 gene"

(ix) FEATURE:
         (A) NAME/KEY: Cleavage-site
         (B) LOCATION:9

(xi) SEQUENCE DESCRIPTION: SEQ ID NO: 5:

Ser Asn Gly Gly Arg Val Lys Cys Met Gln Val Trp Pro Pro Ile Gly
1               5                   10                  15

Lys Lys (2) INFORMATION FOR SEQ ID NO: 6:

(i) SEQUENCE CHARACTERISTICS:
        (A) LENGTH: 18 amino acids
        (B) TYPE: amino acid
```

```
            (C) STRANDEDNESS:
            (D) TOPOLOGY: linear (ii) MOLECULE TYPE: peptide (vi) ORIGINAL SOURCE:
            (A) ORGANISM: chimeric (ix) FEATURE:
            (A) NAME/KEY: Peptide
            (B) LOCATION:1..18
            (D) OTHER INFORMATION:/note= "fusion region of the transit
                peptide from Rubisco small subunit to the NPTII protein"

(ix) FEATURE:
            (A) NAME/KEY: Cleavage-site
            (B) LOCATION:9

(ix) FEATURE:
            (A) NAME/KEY: Region
            (B) LOCATION:17..18
            (D) OTHER INFORMATION:/note= "amino acid residues derived
                from the original NPTII protein"

(xi) SEQUENCE DESCRIPTION: SEQ ID NO: 6:

Ser Asn Gly Gly Arg Val Lys Cys Met Asp Pro Ala Asn Leu Ala Trp
1               5                   10                  15

Ile Glu
```